US009084554B2

(12) United States Patent
Jung et al.

(10) Patent No.: US 9,084,554 B2
(45) Date of Patent: Jul. 21, 2015

(54) MULTI-PHASE PSEUDO-CONTINUOUS ARTERIAL SPIN LABELING

(75) Inventors: Youngkyoo Jung, La Jolla, CA (US); Eric C. Wong, Del Mar, CA (US); Thomas Liu, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 773 days.

(21) Appl. No.: 12/728,170

(22) Filed: Mar. 19, 2010

(65) Prior Publication Data

US 2010/0240983 A1    Sep. 23, 2010

Related U.S. Application Data

(60) Provisional application No. 61/161,735, filed on Mar. 19, 2009, provisional application No. 61/166,177, filed on Apr. 2, 2009.

(51) Int. Cl.
*A61B 5/055* (2006.01)
*A61B 5/02* (2006.01)
*G01R 33/563* (2006.01)
*G01R 33/483* (2006.01)

(52) U.S. Cl.
CPC ............ *A61B 5/055* (2013.01); *A61B 5/02028* (2013.01); *G01R 33/56366* (2013.01); *G01R 33/4833* (2013.01)

(58) Field of Classification Search
USPC .................................................. 600/407–436
See application file for complete search history.

(56) References Cited

U.S. PATENT DOCUMENTS

| 6,271,665 | B1 | 8/2001 | Berr et al. |
| 6,564,080 | B1 | 5/2003 | Kimura |
| 7,587,233 | B2 | 9/2009 | Wong et al. |
| 8,195,274 | B2 | 6/2012 | Wong |
| 2004/0030240 | A1 | 2/2004 | Kimura |
| 2004/0044281 | A1 | 3/2004 | Jesberger et al. |

(Continued)

FOREIGN PATENT DOCUMENTS

| JP | 2005-305151 A | 11/2005 |
| WO | 03/094725 A1 | 11/2003 |

(Continued)

OTHER PUBLICATIONS

Wong, E.C., et al., "Velocity Selective Arterial Spin Labeling using an Adiabatic Hyperecho Pulse Train," Proceedings of the International Society for Magnetic Resonance in Medicine, 11:2181, (2003).

(Continued)

*Primary Examiner* — Mark Remaly
(74) *Attorney, Agent, or Firm* — Perkins Coie LLP

(57) ABSTRACT

Techniques, systems and apparatus are described for magnetic resonance imaging. A magnetic resonance imaging (MRI) system comprises a scanner comprising a magnet, gradient coils and a radio frequency (RF) system to perform various operations. The scanner can apply a gradient field and a train of RF pulses comprising more than two phases to tag a target blood vessel, and acquire magnetic resonance signals based on the applied train of RF pulses to sample the more than two phases. The MRI system includes a data processing system in communication with the scanner to receive the acquired magnetic resonance signals and process the received magnetic resonance signal to generate images proportional to perfusion.

20 Claims, 32 Drawing Sheets

(56) References Cited

U.S. PATENT DOCUMENTS

| | | | |
|---|---|---|---|
| 2004/0162483 | A1 | 8/2004 | Kimura |
| 2005/0277825 | A1 | 12/2005 | Wong et al. |
| 2005/0277828 | A1 | 12/2005 | Alsop |
| 2006/0100503 | A1 | 5/2006 | Takai et al. |
| 2006/0161060 | A1 | 7/2006 | Pai |
| 2006/0184007 | A1 | 8/2006 | Judd et al. |
| 2007/0282193 | A1 | 12/2007 | Brown |
| 2008/0269595 | A1* | 10/2008 | Wong .......................... 600/411 |
| 2009/0088626 | A1 | 4/2009 | Sutton et al. |
| 2010/0030062 | A1 | 2/2010 | Bolar et al. |
| 2012/0268126 | A1 | 10/2012 | Guo et al. |
| 2012/0271157 | A1 | 10/2012 | Wong et al. |
| 2013/0096418 | A1 | 4/2013 | Jung et al. |

FOREIGN PATENT DOCUMENTS

| | | |
|---|---|---|
| WO | 03/094728 A1 | 11/2003 |
| WO | 2011/130581 A2 | 10/2011 |
| WO | 2012/145687 A2 | 10/2012 |
| WO | 2012/145765 A2 | 10/2012 |

OTHER PUBLICATIONS

Wong, E.C., et al., "Velocity Selective Arterial Spin Labeling," Proceedings of the International Society for Magnetic Resonance in Medicine,10:621, (2002).

Wu, W.C., et al., "A theoretical and experimental investigation of the tagging efficiency of pseudocontinuous arterial spin labeling," Magnetic Resonance in Medicine, 58(5):1020-1027, Nov. 2007.

Wu, W.C., et al., "The Effects of Flow Dispersion and Cardiac Pulsation in Arterial Spin Labeling," IEEE Transactions on Medical Imaging, 26(1):84-92, Jan. 2007.

Zaharchuk, G. et al., "Multislice perfusion and perfusion territory imaging in humans with separate label and image coils," Magnetic Resonance in Medicine, 41(6):1093-1098, Jun. 1999.

Zimine, I., et al., "Dual vessel arterial spin labeling scheme for regional perfusion imaging," Magnetic Resonance in Medicine, 56(5):1140-1144, Nov. 2006.

Jung, Y., et al., "Pseudo-continuous arterial spin labeling with optimized tagging efficiency for quantitative ASL fMRI," Proceedings 17th Scientific Meeting, International Society for Magnetic Resonance in Medicine, p. 1578, (2009).

Kim, S.G., et al., "Perfusion imaging by a flow-sensitive alternating inversion recovery (FAIR) technique: Application to functional brain imaging," Magnetic Resonance in Medicine, 37(3):425-435, Mar. 1997.

Lu, K., et al., "Regional white matter perfusion measurement using an optimized pseudo-continuous ASL MRI," Proceedings 17th Scientific Meeting, International Society for Magnetic Resonance in Medicine, p. 1521, (2009).

Parry, A. & P.M. Matthews, "Functional magnetic resonance imaging (fMRI): A 'window' into the brain," Oxford University, Centre for Functional Magnetic Resonance Imaging of the Brain (2002), 42 pages, Web site: http://www.fmrib.ox.ac.uk/fmri_intro/fmri_intro.htm [originally accessed on Aug. 20, 2003].

Van Gelderen, P., et al., "Pittfalls of MRI measurement of white matter perfusion based on arterial spin labeling," Magnetic Resonance in Medicine, 59(4):788-795, Apr. 2008.

Williams, D.S., et al., "Magnetic resonance imaging of perfusion using spin inversion of arterial water," Proceedings of the National Academy of Sciences of the United States of America, 89(1):212-216, Jan. 1992.

Alsop, D.C., et al., "Reduced transit-time sensitivity in noninvasive magnetic resonance imaging of human cerebral blood flow," Journal of Cerebral Blood Flow and Metabolism, 16(6):1236-1249, Nov. 1996.

Brookes, M.J., et al, "Noninvasive measurement of arterial cerebral blood volume using look-locker EPI and arterial spin labeling," Magnetic Resonance in Medicine, 58(1):41-54, Jul. 2007.

Buxton, R.B., et al., "A general kinetic model for quantitative perfusion imaging with arterial spin labeling," Magnetic Resonance in Medicine, 40(3):383-396, Sep. 1998.

Dai, W., et al., "Continuous Flow-Driven Inversion for Arterial Spin Labeling Using Pulsed Radio Frequency and Gradient Fields," Magnetic Resonance in Medicine, 60(6):1488-1497, Dec. 2008.

Davies, N.P., et al., "Selective arterial spin labeling (SASL): perfusion territory mapping of selected feeding arteries tagged using two-dimensional radiofrequency pulses," Magnetic Resonance in Medicine, 49(6):1133-1142, Jun. 2003.

Detre, J.A., et al., "Perfusion imaging," Magnetic Resonance in Medicine, 23(1):37-45, Jan. 1992.

Detre, J.A., et al., "Noninvasive Perfusion MR Imaging Using Spin Labeling Arterial Water," Chapter 15, Part V in Diffusion and Perfusion: Magnetic Resonance Imaging: Applications to Functional MRI (D. Le Bihan, Ed.), p. 296-305, Raven Press, New York, 1995.

Dixon, W.T., et al., "Projection angiograms of blood labeled by adiabatic fast passage," Magnetic Resonance in Medicine, 3(3):454-462, Jun. 1986.

Duyn, J.H., et al., "Simple correction method for k-space trajectory deviations in MRI," Journal of Magnetic Resonance, 132(1):150-153, May 1998.

Edelman, R.R., et al., "Qualitative mapping of cerebral blood flow and functional localization with echo-planar MR imaging and signal targeting with alternating radio frequency," Radiology, 192(2):513-520, Aug. 1994.

Garcia, D.M., et al., "Pseudo-continuous flow driven adiabatic inversion for arterial spin labeling," Proceedings 13th Scientific Meeting, International Society for Magnetic Resonance in Medicine, p. 37, (2005).

Garwood, M., et al., "Advances in Magnetic Resonance—The Return of the Frequency Sweep: Designing Adiabatic Pulses for Contemporary NMR," Journal of Magnetic Resonance, 153(2):155-177, Dec. 2001.

Garwood, M., et al., "Symmetric Pulses to Induce Arbitrary Flip Angles with Compensation for RF Inhomogeneity and Resonance Offsets," Journal of Magnetic Resonance, 94(3):511-525, Oct. 1991.

Gunther, M., "Efficient visualization of vascular territories in the human brain by cycled arterial spin labeling MRI," Magnetic Resonance in Medicine, 56(3):671-675, Sep. 2006.

Gunther, M., et al. "Single-shot 3D imaging techniques improve arterial spin labeling perfusion measurements," Magnetic Resonance in Medicine, 54(2):491-498, Aug. 2005.

Guo, J., et al., "Imaging of Oxygen Extraction Fraction Using Velocity Selective Excitation with Arterial Nulling (VSEAN)," Proceedings of the International Society for Magnetic Resonance in Medicine,18:4057, (2010).

Hendrikse, J., "Flow territory mapping of the cerebral arteries with regional perfusion MRI," Stroke, 35(4):882-887, Apr. 2004.

Hennig, et al., "Hyperechoes," Magnetic Resonance in Medicine, 46(1):Jul. 6-12, 2001.

International Search Report and Written Opinion mailed on Dec. 21, 2011 for International Application No. PCT/US2011/032591, filed Apr. 14, 2011 (7 pages).

International Search Report and Written Opinion mailed on Nov. 30, 2012 for International Application No. PCT/US2012/034537, filed Apr. 20, 2012 (6 pages).

International Search Report and Written Opinion mailed on Nov. 30, 2012 for International Application No. PCT/US2012/034720, filed Apr. 23, 2012 (6 pages).

International Search Report and Written Opinion mailed on Oct. 22, 2010 for International Application No. PCT/US2010/028068, filed Mar. 19, 2010 (7 pages).

International Search Report and Written Opinion mailed on Sep. 15, 2003 for International Application No. PCT/US03/14978, filed May 13, 2003 (3 pages).

Jung, Y., et al., "Multi-phase pseudo-continuous arterial spin labeling (MP PCASL): Robust PCASL method for CBF quantification," Proceedings 17th Scientific Meeting, International Society for Magnetic Resonance in Medicine, p. 622, (2009).

Jung, Y., et al., "Multiphase pseudocontinuous arterial spin labeling (MP-PCASL) for robust quantification of cerebral blood flow," Magnetic Resonance in Medicine, 64(3):799-810, Sep. 2010.

(56) References Cited

OTHER PUBLICATIONS

Kim, S.G., "Quantification of relative cerebral blood flow change by flow-sensitive alternating inversion recovery (FAIR) technique: Application to functional mapping," Magnetic Resonance in Medicine, 34(3):293-301, Sep. 1995.

Kwong, K.K. et al., "Perfusion MR imaging," Proceedings of the Society of Magnetic Resonance, vol. 2, Second Meeting, Aug. 6-12, 1994, San Francisco, California, p. 1005.

Lagarias, J.C., et al., "Convergence properties of the nelder-mead simplex method in low dimensions," SIAM Journal on Optimization, 9(1):112-147, (1998).

Liu, T.T., et al., "A signal processing model for arterial spin labeling functional MRI," NeuroImage, 24(1):207-215, Jan. 2005.

Luh, W.M., et al, "Pseudo-continuous Arterial Spin Labeling at 7T," Proceedings 16th Scientific Meeting, International Society for Magnetic Resonance in Medicine, p. 3339, (2008).

Luh, W.M., et al., "QUIPSS II with thin-slice T1 Periodic Saturation: A Method for Improving Accuracy of Quantitative Perfusion Imaging Using Pulsed Arterial Spin Labeling," Magnetic Resonance in Medicine, 41(6):1246-1254, Jun. 1999.

Mildner, T., et al., "Continuous arterial spin labeling at the human common carotid artery: the influence of transit times," NMR in Biomedicine, 18(1): Feb. 19-23, 2005.

Norris, D.G., et al., "Velocity Selective Radiofrequency Pulse Trains", Journal of Magnetic Resonance, 137 (1):231-236, Mar. 1999.

Paley, R.E.A.C., "On Orthogonal Matrices," Journal of Mathematics and Physics, 12:311-320, (1932-1933).

Sutton, B.P., et al., "Fast, iterative image reconstruction for MRI in the presence of field inhomogeneities," IEEE Transactions on Medical Imaging, 22(2):178-188, Feb. 2003.

Trampel, R., et al., "Efficiency of Flow-Driven Adiabatic Spin Inversion Under Realistic Experimental Conditions: A Computer Simulation," Magnetic Resonance in Medicine, 51(6):1187-1193, Jun. 2004.

Wang, J., et al., "Amplitude-modulated continuous arterial spin-labeling 3.0-T perfusion MR imaging with a single coil: feasibility study," Radiology, 235(1):218-228, Apr. 2005.

Werner, R., et al., "Continuous artery-selective spin labeling (CASSL)," Magnetic Resonance in Medicine, 53 (5):1006-1012, May 2005.

Wong, E.C., "Vessel-encoded arterial spin-labeling using pseudocontinuous tagging," Magnetic Resonance in Medicine, 58(6):1086-1091, Dec. 2007.

Wong, E.C., "Vessel Encoded Arterial Spin Labeling Using Pseudo-Continuous Tagging," Proceedings of the International Society for Magnetic Resonance in Medicine, 14:668, (2006).

Wong, E.C., et al., "Blind detection of vascular sources and territories using random vessel encoded arterial spin labeling," Magnetic Resonance Materials in Physics, Biology and Medicine, 25(2):95-101, Apr. 2012.

Wong, E.C., et al., "Implementation of quantitative perfusion imaging techniques for functional brain mapping using pulsed arterial spin labeling," NMR in Biomedicine, 10(4-5):237-249, Jun.-Aug. 1997.

Wong, E.C., et al., "Quantitative imaging of perfusion using a single subtraction (QUIPSS and QUIPSS II)," Magnetic Resonance in Medicine, 39(5):702-708, May 1998.

Wong, E.C., et al., "Velocity-selective arterial spin labeling," Magnetic Resonance in Medicine, 55(6):1334-1341, Jun. 2006.

* cited by examiner

|  | PICORE ASL | PCASL | Optimized PCASL |
|---|---|---|---|
| $CBF^o$ | 58.6 | 44.9 | 56.5 |
| $\Delta CBF$ | 40 | 29.5 | 39.1 |
FIG. 18
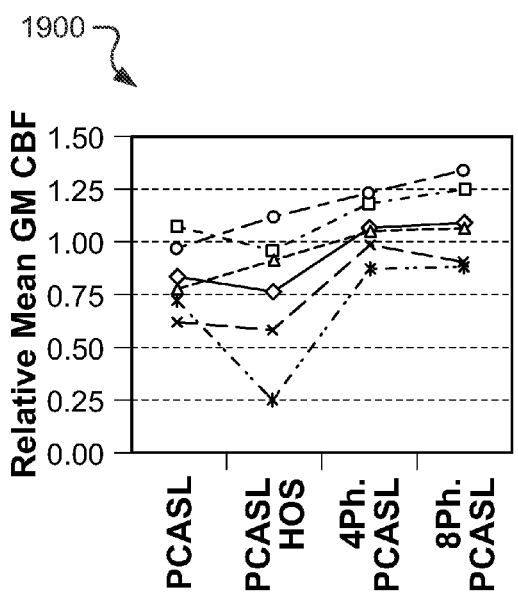
FIG. 19a
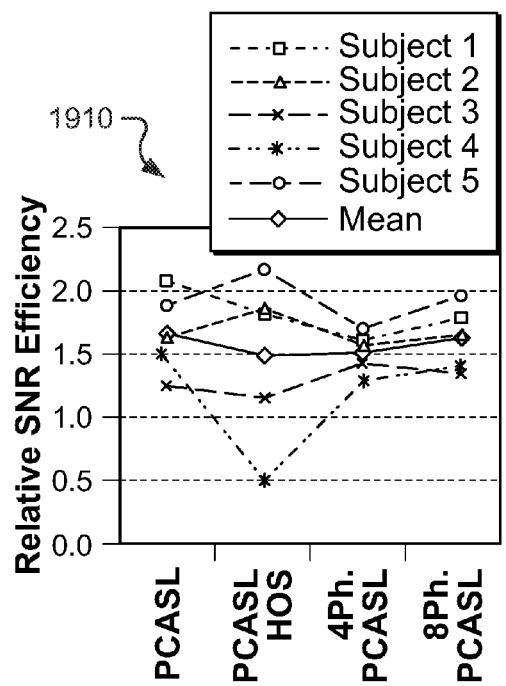
FIG. 19b

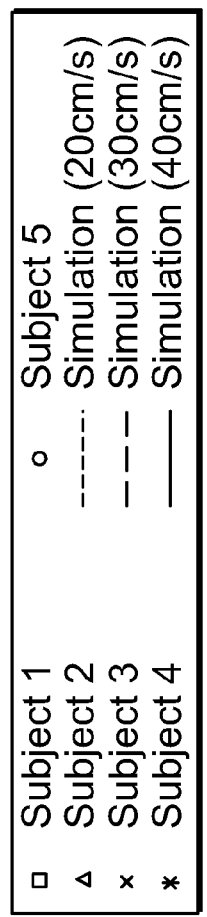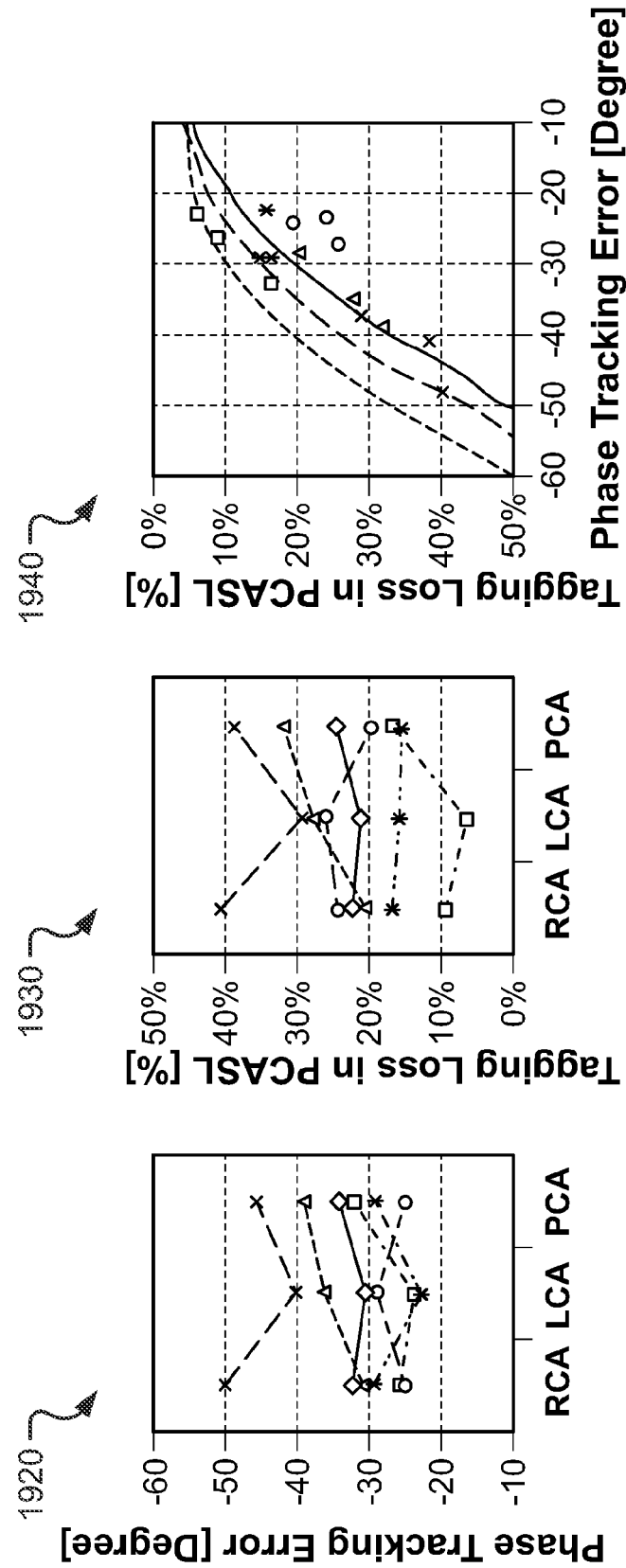
FIG. 19e
FIG. 19d
FIG. 19c

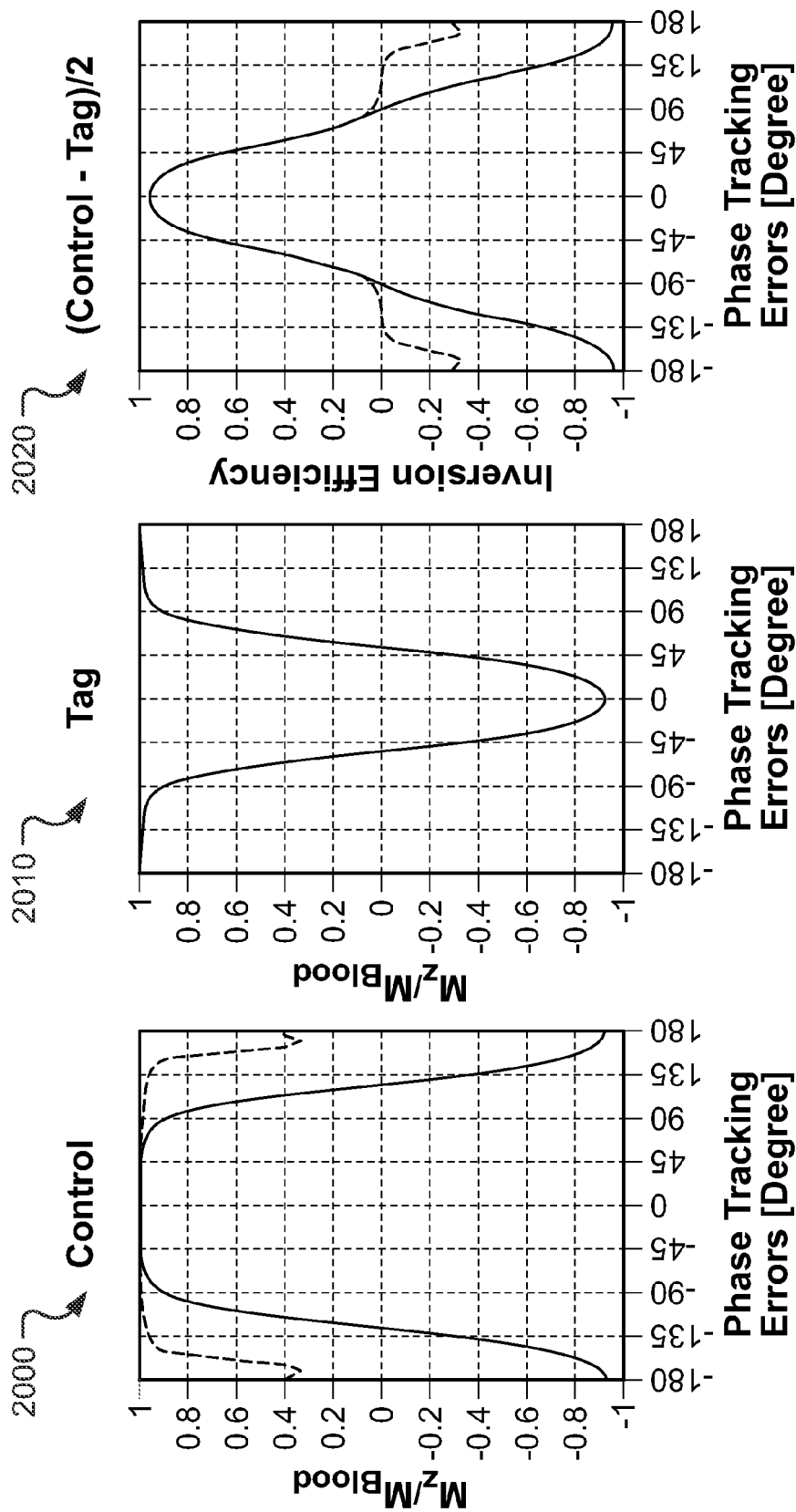

|  | Mean GM CBF (ml/100g tissue/min) | | | Δmean(ε) |
| --- | --- | --- | --- | --- |
|  | Fitting (A) | Demod. (B) | A-B (%) | |
| Subject 1 | 57.8 | 56.0 | -3.11% | -4.7° |
| Subject 2 | 51.1 | 49.4 | -3.33% | -3.3° |
| Subject 3 | 85.6 | 85.4 | -0.23% | -1.3° |
| Subject 4 | 84.3 | 84.2 | -0.12% | -7.5° |
| Subject 5 | 57.2 | 57.1 | -0.17% | -6.5° |
| Mean | 67.2 | 66.4 | -1.16% | -4.7° |

FIG. 24

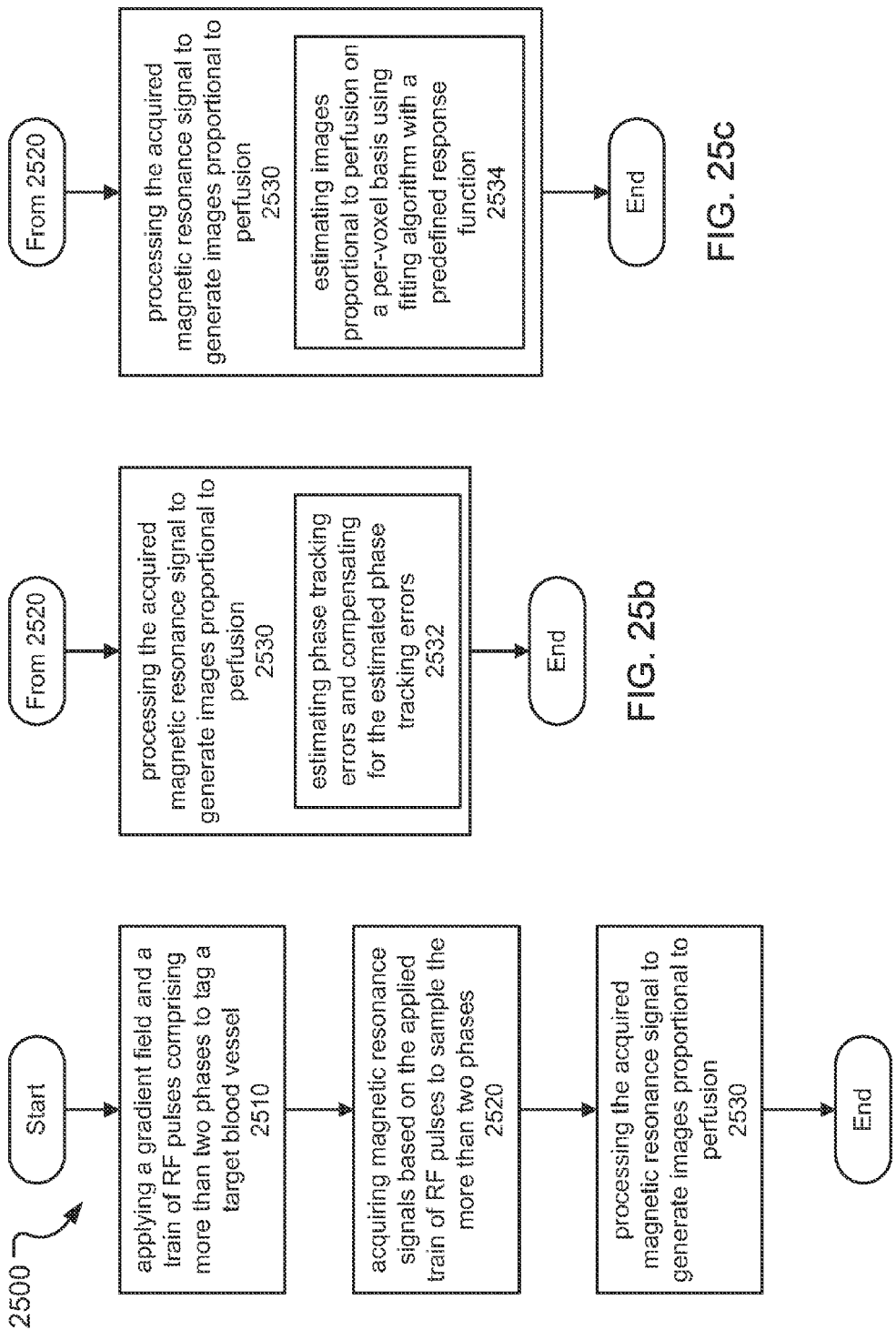

MULTI-PHASE PSEUDO-CONTINUOUS ARTERIAL SPIN LABELING

CLAIM OF PRIORITY

This application claims priority under 35 USC §119(e) to U.S. Patent Application Ser. No. 61/161,735, filed on Mar. 19, 2009, and U.S. Patent Application Ser. No. 61/166,177, filed on Apr. 2, 2009, the entire contents of which are hereby incorporated by reference.

STATEMENT REGARDING FEDERAL RIGHTS

This invention was made with government support under Grant Nos. 5R01EB002096-07 and 5R01NS051661-03 awarded by National Institute of Health. The government has certain rights in the invention.

BACKGROUND

This application relates to techniques, apparatus and systems for magnetic resonance imaging (MRI).

Imaging through MRI techniques is well known and has been widely applied in imaging applications in medical, biological and other fields. In essence, a typical MRI technique produces an image of a selected body part of an object under examination by manipulating the magnetic spins in a body part and processing measured responses from the magnetic spins. A MRI system may include hardware to generate different magnetic fields for imaging, including a static magnetic field along a z-direction to polarize the magnetic spins, gradient fields along mutually orthogonal x, y, or z directions to spatially select a body part for imaging, and an RF magnetic field to manipulate the spins.

MRI techniques may be used to capture the functional changes in body parts or tissues such as the brain perfusion. One commonly-used technique for functional MRI is in vivo imaging by arterial spin labeling (ASL), where the arterial blood is tagged by magnetic inversion using RF pulses applied to a plane or slab of arterial blood proximal to the tissue of interest. Images are typically acquired with and without prior tagging of arterial blood and are subtracted to produce images that are proportional to perfusion. This magnetic tagging allows for the imaging of blood flow without the administration of dyes or other imaging agents. Hence, ASL provides non-invasive tagging in MRI measurements. Examples of pulsed ASL include Proximal Inversion with a Control for Off-Resonance Effect (PICORE) [4] and Flow-sensitive Alternating Inversion Recovery (FAIR) [5].

SUMMARY

Techniques, systems and apparatus are described for implementing multi-phase (more than two) pseudo-continuous arterial spin labeling (MP-PCASL) method for MRI.

In one aspect, MP-PCASL tagging scheme is implemented. The MP-PCASL tagging scheme can be generalized in the equation below, where M represents the total number of phases.

$$\Delta\theta_m = \theta_{n,m} - \theta_{n-1,m} = \gamma Gtd + 2\pi m/M$$

Examples using 4 and 8-phases tagging scheme are described and compared to several conventional ASL methods.

In another aspect, fitting algorithms for signal estimation is implemented. Two algorithms are described as examples: formula (a) takes longer (~5 min) to calculate but provides more accurate estimation on a per-voxel basis than formula (b). The calculation for formula (b) only takes (<1 sec) and can be used when a fast processing is needed.

In yet another aspect, optimization of 2P-PCASL is implemented by adding MP-PCASL and XY shim gradient compensation. The conventional 2P-PCASL can be optimized for the applications listed below which need the higher SNR and/or higher temporal resolution of 2P-PCASL. A short scan is performed first using MP-PCASL to obtain error correction estimation, followed by 2P-PCASL with phase errors corrected using the estimate. Secondly, the different phase errors across blood vessels are compensated by adding small XY shim gradient during labeling (this part is disclosed in SD2007-283, but only for the purpose of vessel encoding, not in combination with MP-PCASL for optimization of non-vessel encoded PCASL). (1) Temporal mode scanning, e.g. fMRI. (2) Obtaining higher SNR, when the SNR gain is calculated to be worth the investment of time to collect the initial MP-PCASL scan. (3) When MP-PCASL is combined with 2P-PCASL in an adaptive manner such that the scanner automatically transitions from MP mode to 2P mode.

The MP-PCASL is applicable to both symmetric (same gradients for control and tag) and asymmetric (different gradients for control and tag) tagging schemes. Symmetric PM-PCASL tagging scheme can be used for both global and territory perfusion imaging, while asymmetric PM-PCASL can only be used for the global perfusion imaging. Besides brain, it is applicable to other organs, such as heart, kidney, lung, and other.

In yet another aspect, a method of magnetic resonance imaging (MRI) includes operations performed by a MRI system. The method includes applying a gradient field and a train of RF pulses that include more than two phases to tag a target blood vessel. The method includes acquiring magnetic resonance signals based on the applied train of RF pulses to sample the more than two phases. Additionally, the method includes processing the acquired magnetic resonance signal to generate images proportional to perfusion.

Implementations can optionally include one or more of the following features. The train of RF pulses can include at least four different phases with an evenly distributed phase offset. Processing the acquired magnetic resonance signals can include estimating phase tracking errors and compensating for the estimated phase tracking errors. Processing the acquired magnetic resonance signal can include estimating images proportional to perfusion on a per-voxel basis using fitting algorithm with a predefined response function. Processing the acquired magnetic resonance signal can include using the fitting algorithm to generate maps that represent a modulated arterial spin labeling (ASL) signal, a phase tracking error and baseline signal. Processing the acquired magnetic resonance signal comprising applying a sinusoidal demodulation. Processing the acquired magnetic resonance signal can include measuring phase tracking errors by setting region of interest (ROI) and calculating average of the measured phase tracking errors in a left hemisphere, a right hemisphere and a posterior area. The method can include compensating for the measured phase tracking error by adding a constant phase offset to a labeling RF pulse. Compensating for the measure phase tracking error can include using XY shim gradient compensation to compensate for asymmetric tagging efficiency. Processing the acquired magnetic resonance signal can include estimating images proportional to perfusion on a per-voxel basis using a fitting algorithm that performs an estimation of a fitting curve to identify an optimum fitting curve in place of a predefined response function. Processing the acquired magnetic resonance signal can include estimating images proportional to perfusion on a per-voxel basis by demodulating a multi-phase frequency component of the received magnetic resonance signal.

In yet another aspect, a method of performing magnetic resonance imaging includes applying a control pulse sequence that includes a train of radio frequency (RF) pulses. The train of RF pulses includes a gradient, RF amplitude waveforms, and an RF phase schedule. The method includes applying a tag pulse sequence that includes another train of RF pulses. The other train of RF pulses includes the gradient, the RF amplitude waveform, and another RF phase schedule different from the FR phase schedule for the control pulse sequence.

The methods described herein can be performed by an MRI system or apparatus. Additionally, the techniques, systems and apparatus as described in this specification can provide one or more of the following advantages. MP-PCASL can provide consistent tagging efficiency resulting in more robust and accurate blood perfusion quantification than the conventional 2-phase (2P) PCASL. The tagging efficiency is enhanced by use algorithms to derive an estimate from the MP PCASL to correct the errors in the phase tracking.

BRIEF DESCRIPTION OF THE DRAWINGS

FIG. 18 is a table that shows Baseline CBF (CBF0) and the changes of CBF ($\Delta$CBF) from three ASL fMRI methods.

FIGS. 19a and 19b show relative mean gray matter CBF values and SNR efficiencies for different PCASL methods normalized to the values from FAIR ASL (lines indicate the simulations at different arterial velocities).

FIGS. 19c and 19d show measured phase tracking errors and tagging losses in the conventional PCASL method for three vascular territories, supplied by the right carotid artery (RCA), the left carotid artery (LCA), and the posterior cerebral artery (PCA) (lines indicate the simulations at different arterial velocities).

FIG. 19e shows a scatter plot of tagging losses to phase tracking errors across subjects and vascular territories (lines indicate the simulations at different arterial velocities).

FIGS. 20a, 20b, and 20c show simulated inversion responses of control and tag conditions and inversion efficiencies for non-zero mean gradient control (solid line) and zero mean gradient control (dash line) as a function of the phase tracking error.

FIG. 24 is a table showing comparisons of mean gray matter CBF and the difference in mean phase tracking errors ($\Delta$mean($\epsilon$)).

FIGS. 25a, 25b, 25c, 25d, 25e, 25f, 25g, 25h, 25i and 25j are process flow diagrams describing processes of performing a MP PCASL method as described in this specification.

Like reference symbols and designations in the various drawings indicate like elements.

DETAILED DESCRIPTION

The techniques, systems and apparatus are described for implementing Multi-Phase Pseudo-Continuous Arterial Spin Labeling (MP PCASL) Magnetic Resonance Imaging (MRI). MP PCASL is a new PCASL method with multiple phases (more than two) offsets. MP PCASL is less sensitive to factors that cause tagging efficiency error in PCASL and result in perfusion quantification errors. The multi-phase PCASL (MP PCASL) method can also be used to estimate the phase tracking errors in the acquisition and includes the correction method of the conventional PCASL method based on the estimated phase tracking errors.

The conventional Arterial Spin Labeling or Tagging (ASL or AST) method measures blood perfusion by the subtraction of tag and control whereas MP PCASL estimates the ASL signal by a fitting algorithm or a sinusoidal demodulation. The PCASL method offers higher SNR than pulsed ASL (PASL). In addition, PCASL can be implemented without the need for a special RF system, which is often required for continuous ASL (CASL). However, PCASL does not provide robust perfusion values in the physiological unit because the tagging efficiency of PCASL can be significantly modulated by both gradient imperfections and the presence of off-resonance fields at the tagged vessels.

Figure 1A:
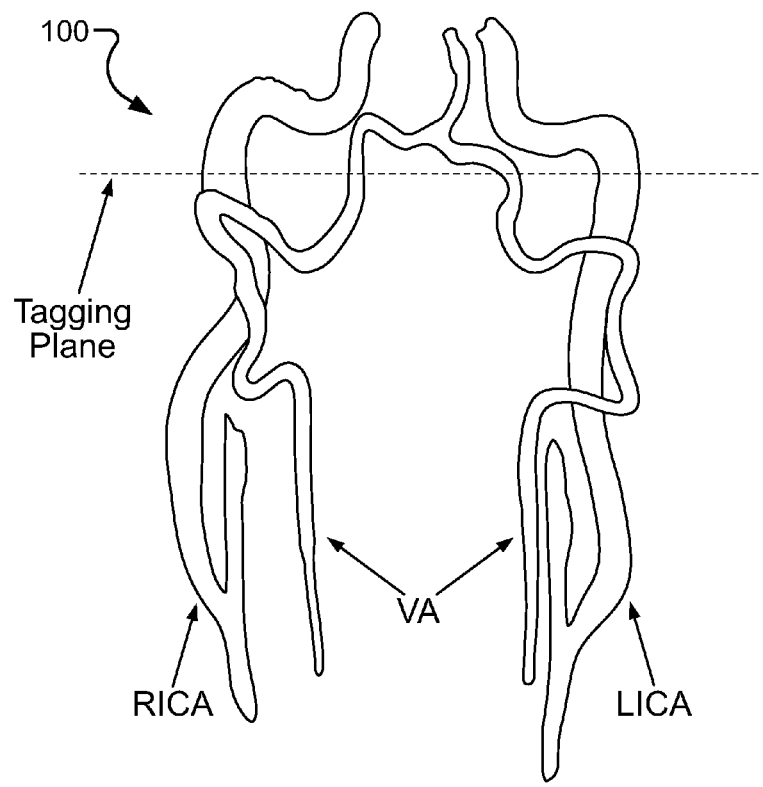
FIG. 1a shows an exemplary tagging plane.

The conventional PCASL tagging method generates tagging of blood in the vessel passing through a tagging plane with RF pulse trains and non-zero mean gradient field which induce flow driven adiabatic inversion of blood. FIG. 1a is a diagram 100 that shows a tagging plane for PCASL, which is typically located below the circle of Willis and tagging RF pulses invert flowing arterial spins in the internal carotid arteries and the vertebral arteries. The flow driven inversion can be achieved by the successive RF pulses when the RF pulse and the spins at the tagging plane are in phase. The RF pulse train in control of PCASL is identical to the labeling (inversion of blood) but its phase is opposite to the spin phase. There are two types of control acquisitions based on the mean of applied gradients: One is with zero mean (named asymmetric tagging method) and the other is with nonzero mean which has same gradient as tag (named symmetric tagging method).

Figure 1B:
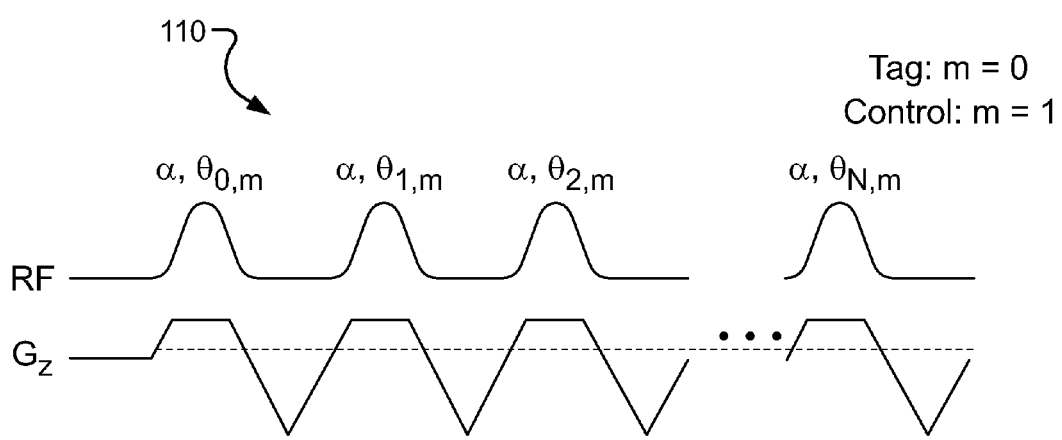
FIG. 1b shows an example pulse diagram of tagging module of PCASL.

The MP PCASL described in this specification utilizes the symmetric tagging method of the conventional PCASL using more than two phases. The pulse diagram of tagging module 110 is shown in FIG. 1b. In addition, MP PCASL can be applied to asymmetric tagging method as described further below.

It is important to consider the phases of RF pulse and spins at the tagging location because the tagging efficiency is tightly tied with those phases. The phase of each RF pulse can be described as a sum of two terms which are a tracking phase and an offset phase as follow:

$$\theta = \theta_{track} + \theta_{offset} \quad (1)$$

The tracking phase ($\theta_{track}$) accounts for the phase accumulated between two successive RF pulses due to the presence of non-zero mean gradient. The tracking phase can maintain the RF phase in phase with the spin and the tracking phase of nth RF pulse can be expressed by $$\theta_{track\ n} = \gamma G T d n, \ n=1,2,\ldots,N \quad (2)$$

where $\gamma$ is the gyromagnetic ratio, G is the average gradient strength, T is the duration between successive RF pulses, d is the distance from the gradient center to tagging location, n denotes the nth RF pulse, and N is the total number of RF pulse train in a tagging module. The offset phase ($\theta_{phase}$) describes the labeling or control condition and the offset phase of nth RF pulse and a tagging status can be expressed by $$\theta_{offset\ n,m} = \pi m n, \quad (3)$$

where n=1, 2, ..., N and m=0 (for labeling) or 1 (for control). The labeling pulse has zero phase offset to keep in phase with the spins in the tagging plane, whereas those in the control state have a phase increment $\pi$ to create a transparent pulse train. Combining above relations, the phase ($\theta_{n,m}$) of the nth RF pulse in the mth state can be represented by:

$$\theta_{n,m} = \theta_{track\ n} + \theta_{offset\ n,m} = \gamma G T d n + \pi m n \quad (4)$$

and a corresponding phase increment ($\Delta\theta_m$) between two RF pulse is $$\Delta\theta_m = \theta_{n,m} - \theta_{n-1,m} = \gamma G T d + \pi m \quad (5)$$

Sources of Error in the Conventional PCASL

Figure 1D:
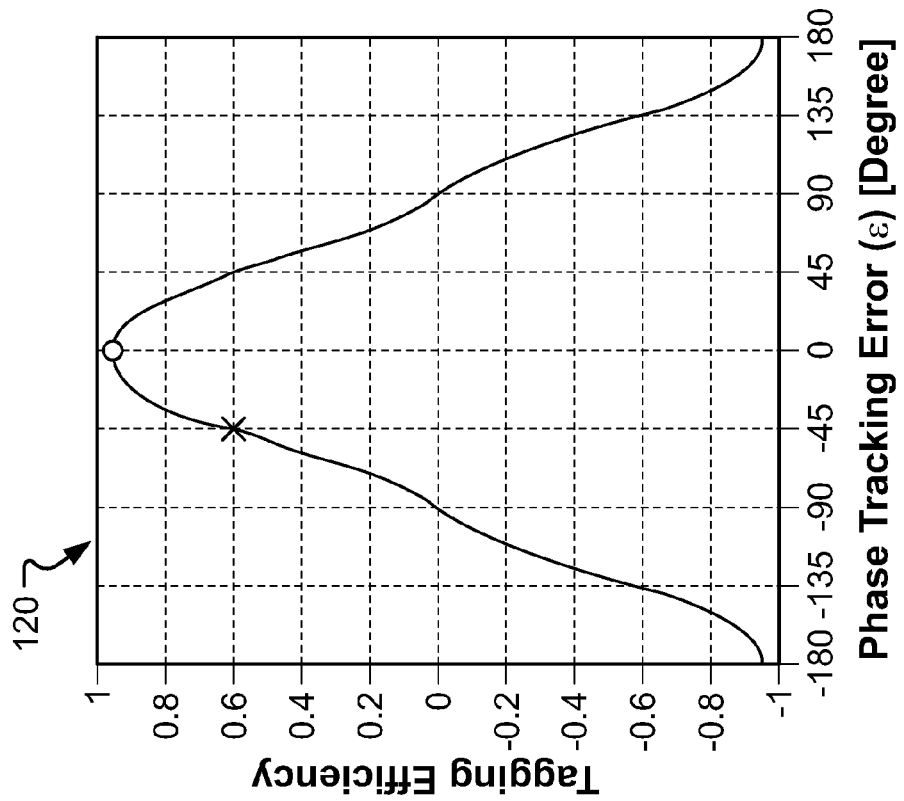
FIG. 1d shows the tagging efficiency to phase tracking errors.
Figure 1C:
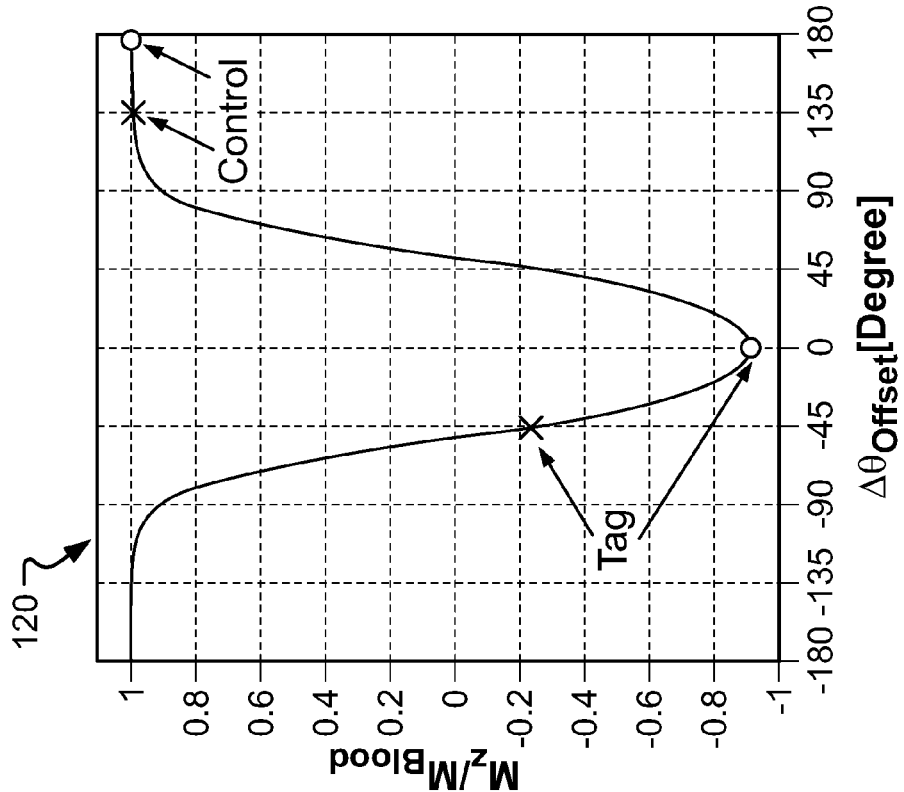
FIG. 1c shows a simulated inversion response to the phase offset without the phase tracking errors.

The knowledge on RF pulse phase is needed to ensure the predictable tagging efficiency, which can be represented as the ratio of the blood magnetization difference between the control and tag conditions to the ideal difference between fully relaxed and perfectly inverted magnetization. FIG. 1c shows the calculated inversion response curve as a function of phase offset, with the net magnetizations of the tag and control conditions indicated by the circles on the inversion response curve at offsets of 0 and 180 degrees, respectively. The tagging efficiency is maximized for this case, as shown by the circle in FIG. 1d.

When errors in the tracking phase ($\epsilon$) exists, the phase increment in Eq. 5 has additional term as follows $$\Delta\theta_m = \gamma G t d + \epsilon + \pi m \quad (6)$$

The presence of a tracking error shifts the positions of the tag and control conditions along the inversion response curve. FIG. 1c shows a simulated inversion response as a function of phase offset. Circles indicate tag and control conditions with no phase tracking error; crosses correspond to −45° phase tracking errors.

Because the symmetric tagging method is considered, the phase tracking error is common in both the labeling pulse and the control pulse, and the phase tracking error causes shift of both the labeling and the control with same amount of phases. FIG. 1d shows the tagging efficiency to phase tracking errors. When the predefined tracking phase has errors, the desired tagging efficiency may not be achieved. For example, if there is a 90° phase tracking errors, the tagging efficiency becomes zero. The possible sources bringing the phase tracking errors are off-resonance at the tagged vessel and gradient imperfections. Typically the tagging plane locates below the circle of Willis and the tagging pulse tags bloods in the internal carotid arteries and vertebral arteries. The off-resonance frequencies at these regions are often too big to be negligible especially at higher field strength (3T or higher).

Figure 2A:
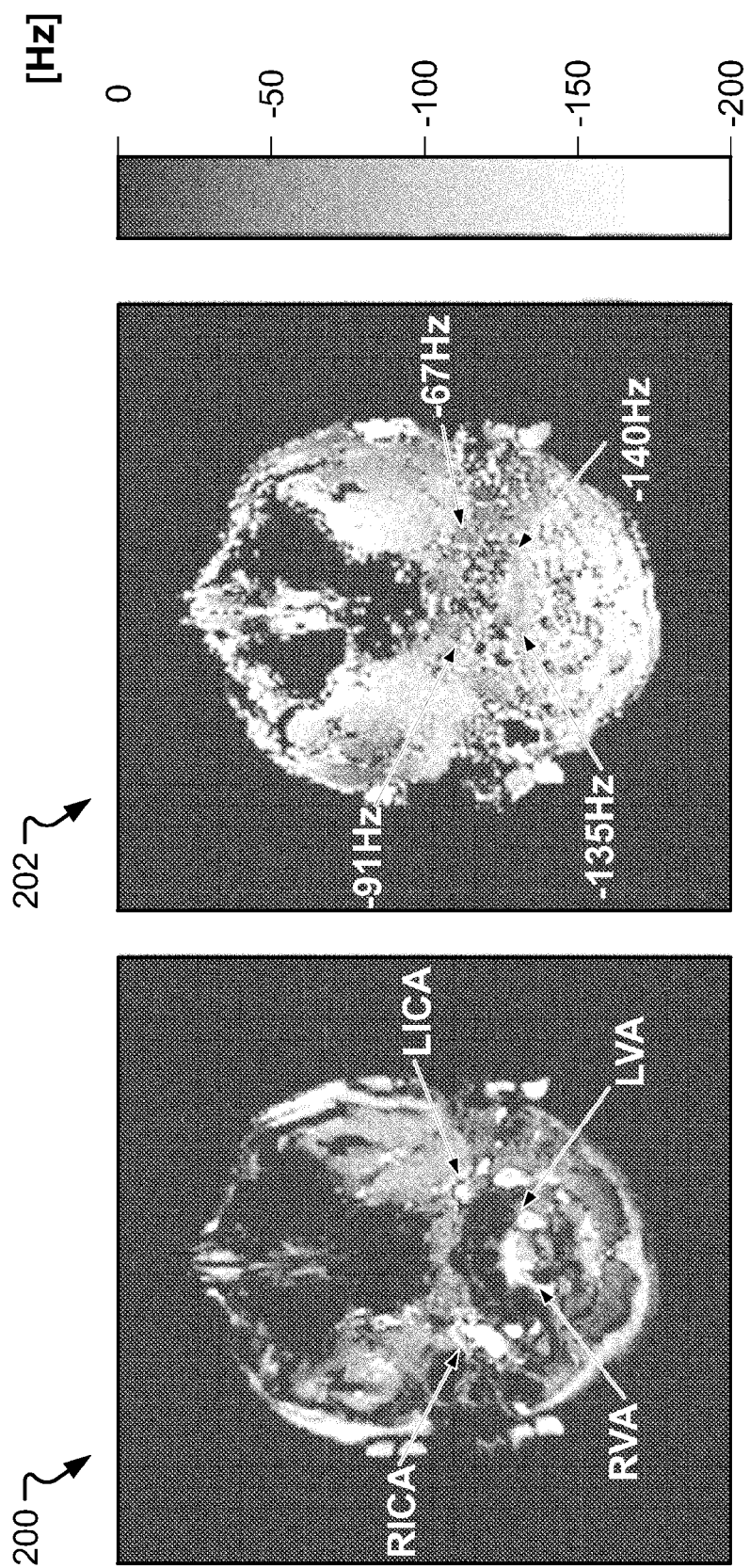
FIG. 2a shows the magnitude image (left) and the field map (right) acquired at the tagging plane.
Figure 2B:
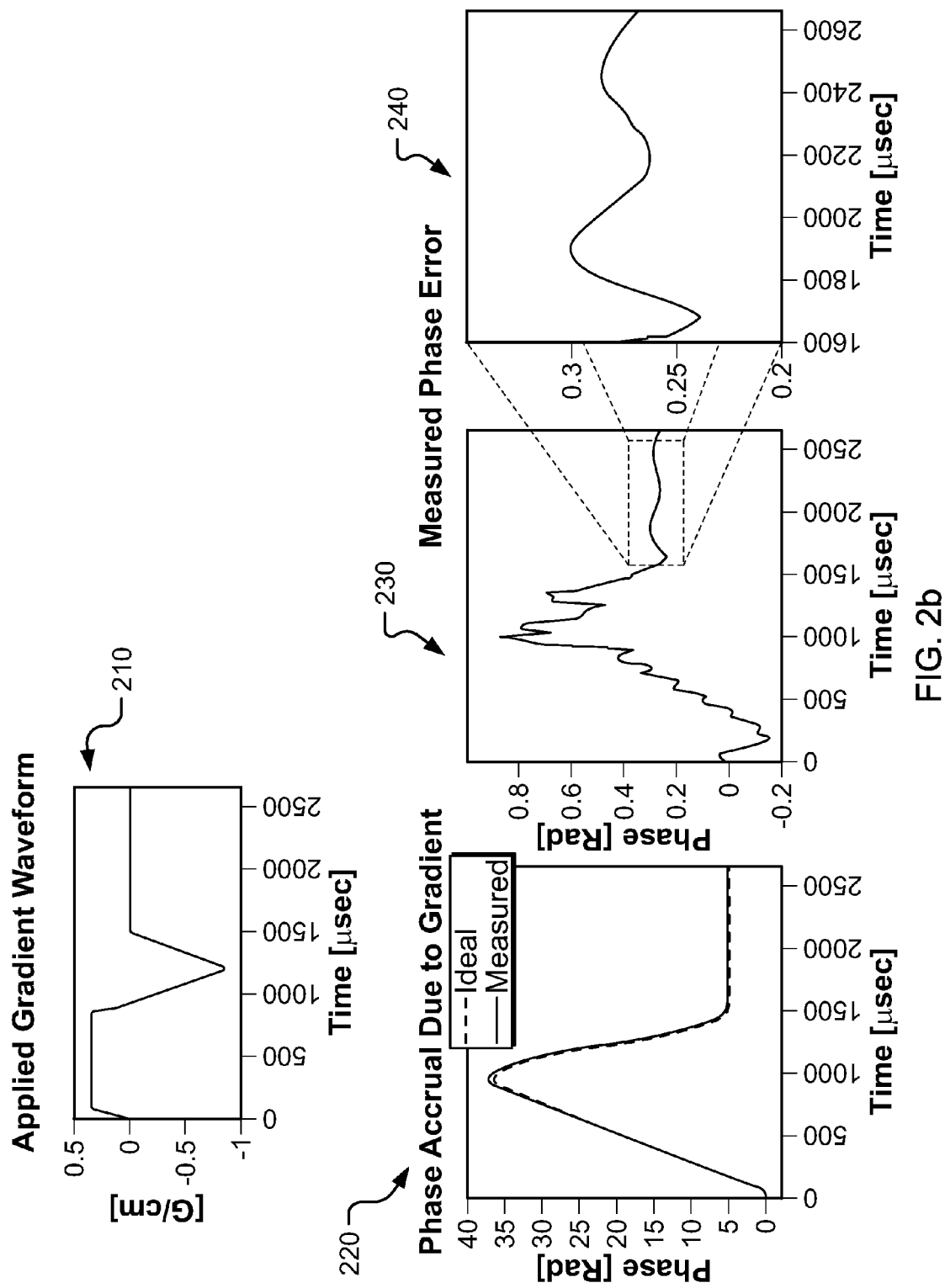
FIG. 2b shows measured phase error due to gradient imperfection (middle) and the enlarged showing the oscillation of errors due to long-term eddy current (right).

Example sources of phase tracking errors due to off-resonance fields and gradient imperfections are shown in FIGS. 2a and 2b. The phase tracking errors due to off-resonance fields at the major arteries in a subject are indicated in FIG. 2a. FIG. 2a shows the magnitude image (left, 200) and the field map (right, 202) acquired at the tagging plane. The major arteries supplying the blood to the brain, such as the right internal carotid artery (RICA), the left internal carotid artery (LICA), the right vertebral artery (RVA), and the left vertebral artery (LVA), are labeled in the magnitude image. The corresponding off-resonance frequencies at the major arteries are indicated. These values are high enough to cause substantial loss of tagging efficiency (see FIG. 1d), with different off-resonance fields and hence tagging efficiencies at each artery.

FIG. 2b shows the phase accrual 220 due to the applied gradient 210 and the corresponding phase errors due to gradient imperfections. The phase errors were measured in an agar phantom at 2 cm below the gradient center to avoid phase unwrapping errors and converted to the errors at 8 cm below the gradient center, where the tagging plane was typically located for the in-vivo experiments, under the assumption that the induced magnetic fields are linear. The measures indicated that the applied gradients resulted in a phase tracking error of approximately 57 degrees at the end of a single RF pulse period. The residual long-term eddy currents are shown in the magnified section 240 in FIG. 2b. Because the eddy current effect persists over next RF pulse period, accurate measurement of the actual phase tracking errors using a single RF pulse has limited application.

Multi-Phase PCASL Tagging Scheme

Figure 3:
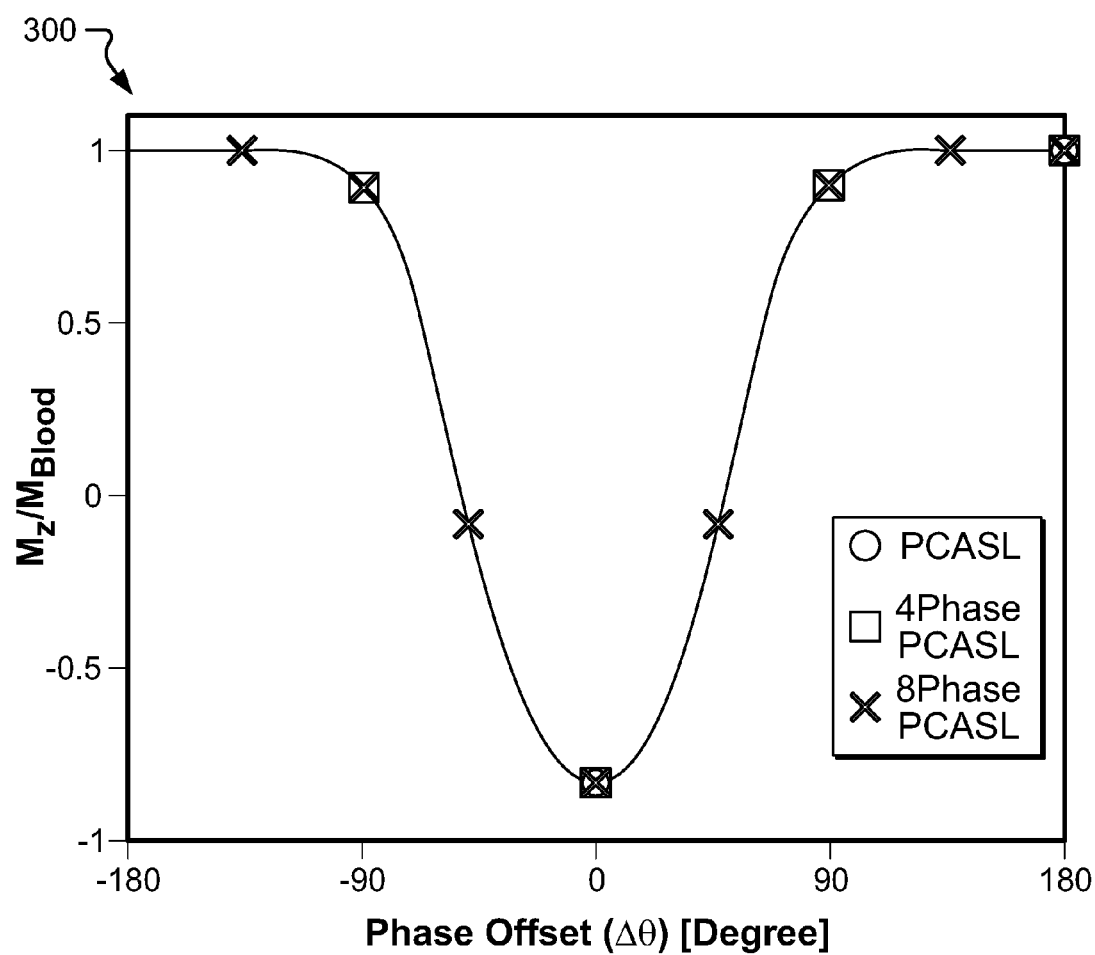
FIG. 3 shows simulated inversion response to the phase offset.

Acquiring multiple phases reduces sensitivity to the phase tracking errors because it allows the acquired data to be fit to a predefined inversion response function. Evenly distributed offset phase is tested and Eq. 5 can be generalized for multiple phase tagging scheme as follows:

$$\Delta\theta_m = \theta_{n,m} - \theta_{n-1,m} = \gamma G t d + 2\pi m/M \quad (7)$$

where M represents the total number of phases. The conventional PCASL method has the M of 2 for the labeling and the control which have offset phase increment of 0 and $\pi$, respectively. Four- and eight-phase tagging schemes are used, which have evenly distributed phase offsets of $\pi/2$ and $\pi/4$, respectively. For example, the phase offset of 4 phase PCASL is 0°-90°-180°-270°. FIG. 3 shows the phase offsets on the inversion response for 4 and 8 phase PCASL methods. The acquired offset points for each method are indicated.

Signal Estimation in MP PCASL

The perfusion signal can be estimated on a per-voxel basis using fitting algorithm with a predefined response function. The measured signal from $i^{th}$ voxel at $m^{th}$ offset phase ($\theta_{offset\ m}$) to be fitted, $s_{i\ m}$, can be expressed by $$S_{i\ m} = p_i f(\theta_{offset\ m} - \epsilon_i) + b_i \quad (8)$$

where $p_i$ is the ASL signal modulated by tagging, $f(\theta_{offset\ m} - \epsilon_i)$ is the fitting function which represents the perfusion modulation, $\epsilon_i$ is the phase tracking errors, and $b_i$ is the baseline signal from the static tissue common in all multiple tagging scheme.

Figures 4A, 4B, 4C:
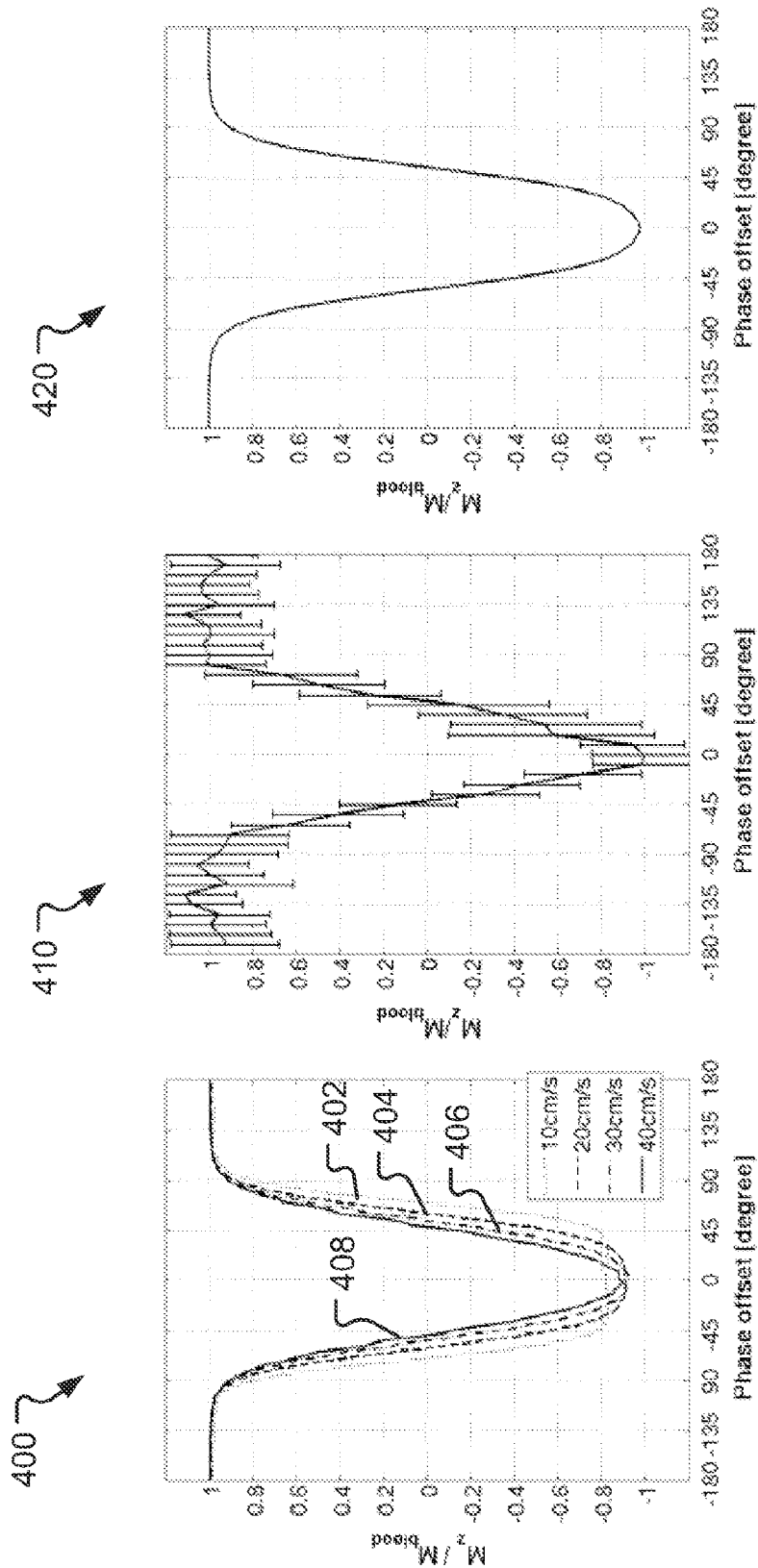
FIGS. 4a-c show inversion response curves to phase offset in PCASL.

FIGS. 4a-c show various data charts 400, 410 and 420 of the simulated and measured inversion response curves to phase offset in PCASL and a proposed fitting function. Bloch simulation is performed with the inversion response with the blood velocity range of 10 to 40 cm/s and the resulting curves (402, 404, 406 and 408 respectively) are presented in FIG. 4a. Forty offset phases are played to measure the inversion response of PCASL. The ROI is selected in the gray matter in the left hemisphere and contained 221 voxels. The curves from each voxel scaled from +1 to −1 and their phase tracking errors also compensated in order to generate the mean curve in FIG. 4b. The example of fitting function is a modified Fermi function which is expressed by $$f(x) = -2\left[\frac{1}{1+e^{(|x|-\alpha)/\beta}}\right]+1 \quad (9)$$

FIG. 4c shows the proposed fitting curve with $\alpha$ of 54 and $\beta$ of 13 that provided the best fit to the inversion response at 30 cm/s (normalized RMS error of 0.8%). The normalized RMS error, which is the RMS error divided by the range of observation (here it was 2), between the fitting curve and the measured response in FIG. 4b was 9.1%.

The voxel-based values in Eq. 8 can be estimated by a fitting method, such as an unconstraint nonlinear optimization method. In order to accelerate the fitting algorithm, the initial values on the fitting algorithm can be set as a half of difference of maxima and minima of the multi-phase signals for the ASL signal, median of the multi-phase signals for the baseline, and the phase of the minima for the initial phase tracking error.

Figure 5:
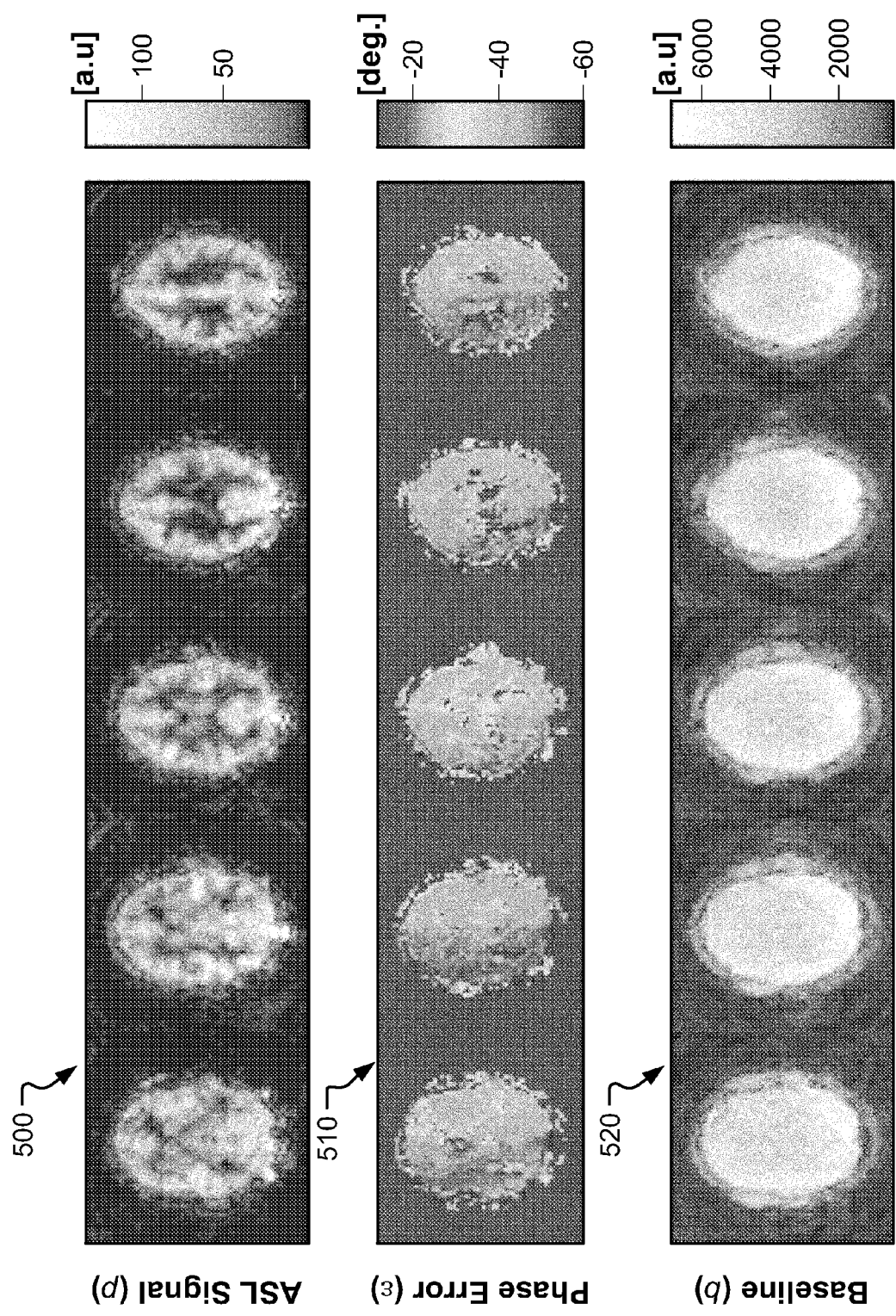
FIG. 5 shows results from proposed fitting method.

FIG. 5 shows results 500, 510 and 520 from proposed fitting method. The fitting algorithm generates three maps which represent the modulated ASL signal, the phase tracking error, and the baseline signals. MP PCASL method can provide the ASL signal estimate (first row). In addition to the ASL signal, the fitting algorithm provides estimates of the phase tracking errors on a per-voxel basis. These errors should be uniform across each vascular territory, providing additional opportunities for robust estimation (second row).

The fitting algorithm needs long estimation time (~5 min.). Another ASL signal calculation method is a sinusoidal demodulation under assumption that the inversion response is a sinusoidal function. The ASL acquisition has multiple repetitions because of its low SNR. The time course at each voxel which has elements of T contains a unique frequency component which is modulated by the multi-phase acquisition. Demodulation of the time course based on the number of phase can provide fast calculation method (<1 sec). The demodulation equation provides the complex form of perfusion signal. Its magnitude is the estimated ASL signal and the phase is the phase tracking errors. The demodulation is described in Eq. 10.

$$\vec{p}_i = \sum_{t=1}^{T} s_{i,t} e^{-j(2\pi t/M + \pi)}, \quad (10)$$

$$p_i = |\vec{p}_i|,$$

$$\epsilon_i = \arg(\vec{p}_i)$$

Figure 6:
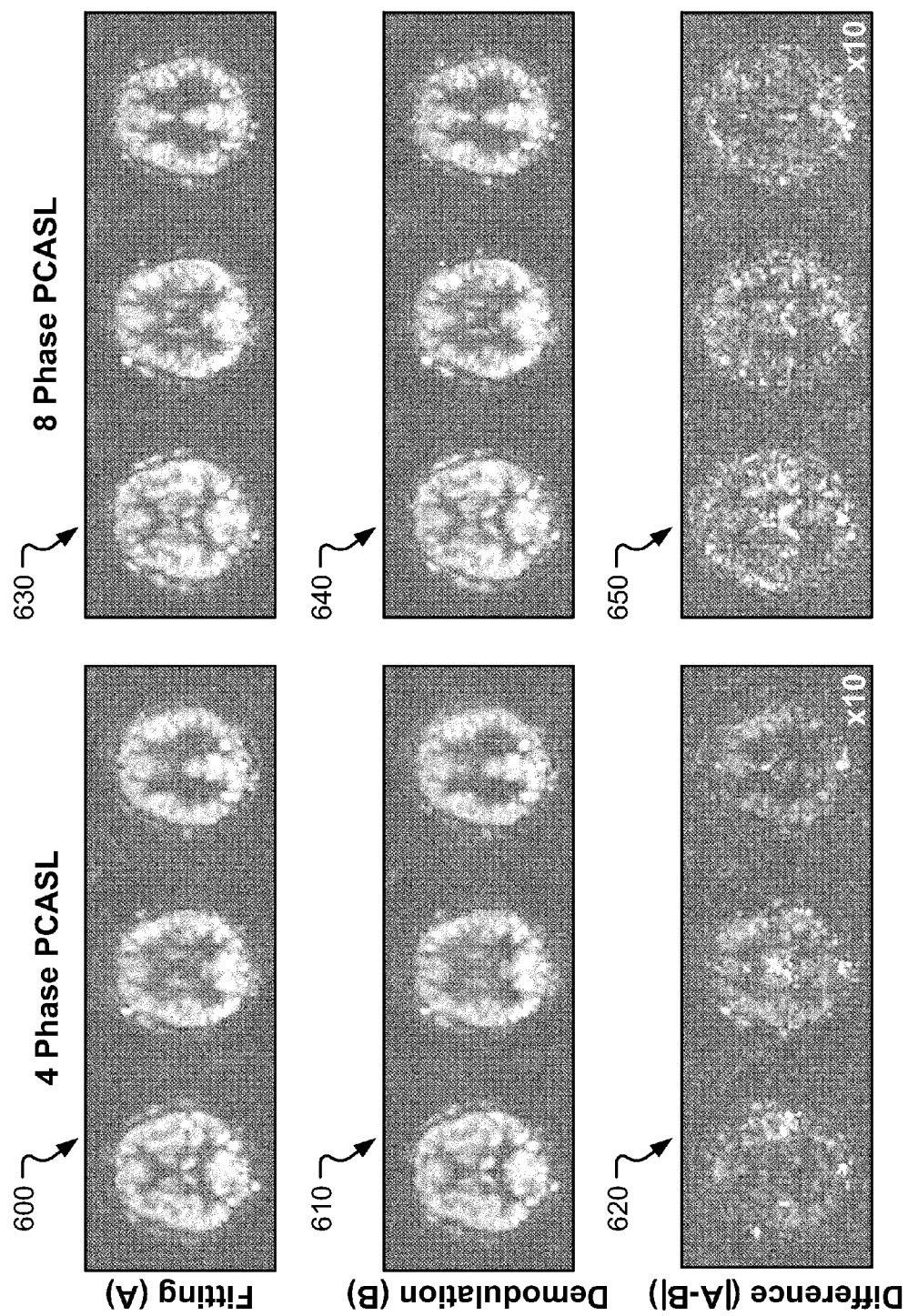
FIG. 6 shows the comparison of ASL signal difference between two estimation methods.

FIG. 6 shows the comparison of ASL signal difference between two estimation methods: 4 Phase PCASL (600, 610 and 620) and 8 Phase PCASL (630, 640 and 650). Both method shows similar estimated ASL signal. The differences of two estimation methods are shown in last row (620 and 650) and are scaled up by 10 to make them visible. The fitting method could be more accurate since it uses the fitting function which is closer to actual inversion response than an inverted cosine function. However, the demodulation described in this specification has much shorter processing time so it could be an alternative method when fast processing is needed.

Optimization Method of the Conventional PCASL

The multi-phase method can provide robust perfusion estimation. However, it may not be an optimal way especially for fMRI application because temporal resolution of fMRI acquisition depends on the scan time for one set of phases (4 or 8 phases are required instead of 2). And SNR of MP PCASL method is lower than that of the conventional PCASL which does not have the phase tracking error. Therefore correction the phase tracking errors in conventional PCASL will be beneficial especially in the application the optimal SNR is required but additional a few minutes of tagging tuning is allowed. This optimization technique includes the use of MP PCASL method as a phase tracking error measurement because it enables the estimation of the phase errors as well as the perfusion signal on a per-voxel basis. The phase tracking errors in the internal carotid arteries and basilar arteries (or vertebral arteries) can be estimated by setting ROI and calculating averages of the phase tracking errors in the left hemisphere, the right hemisphere, and the posterior area, respectively. The estimated phase error which is global through a tagging plane can then be compensated by adding a constant phase offset to the labeling RF pulses ($\Delta\theta_m$ in Eq. 6) to cancel the error term out. However, the labeling plane typically contains several blood vessels, each of which may have a different phase error due to the local field frequency offset, causing non-uniform tagging efficiency across blood vessels.

Figure 7:
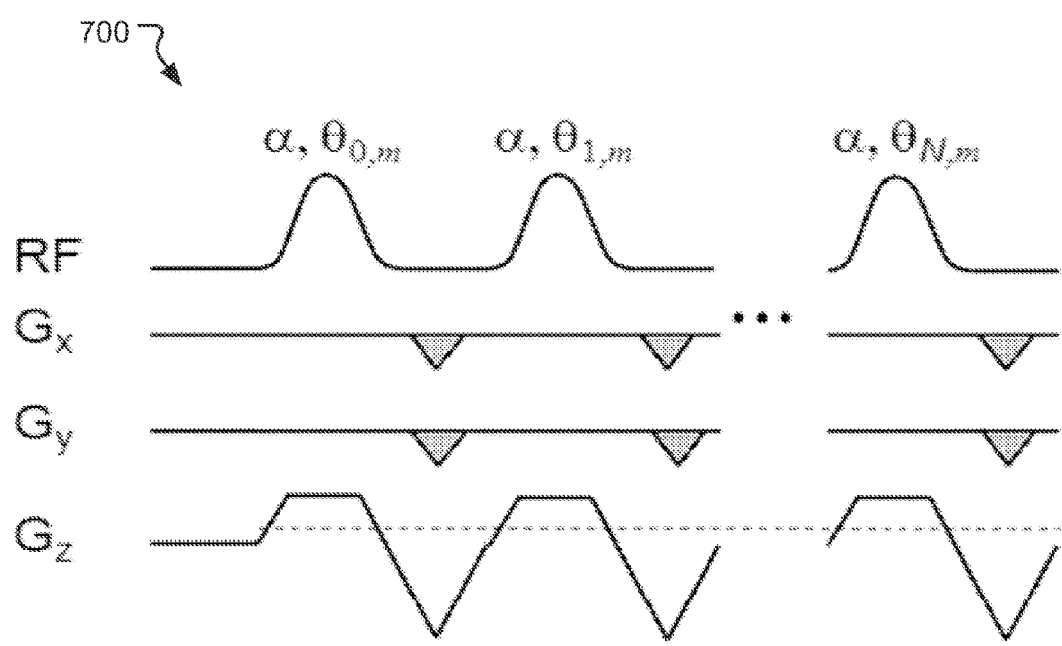
FIG. 7 shows a diagram of tagging modulation with the additional phase offset ($\Delta\theta$) and compensation gradients expressed by the shaded area in $G_x$ and $G_y$.

This asymmetric tagging efficiency can be compensated by adding gradients in x and y plane (shaded gradient area in FIG. 7).

FIG. 7 shows a diagram 700 of tagging modulation with the additional phase offset (Δθ) and compensation gradients expressed by the shaded area in $G_x$ and $G_y$. A uniform and near-optimal tagging efficiency across all tagged vessels can be achievable.

MP PCASL for Asymmetric Tagging Scheme

Asymmetric tagging scheme has identical RF and gradients in labeling but zero-mean gradient in control. The multiphase acquisition concept is not limited to the symmetric tagging scheme but can be also applied to the asymmetric tagging scheme by collecting multiple labeling acquisition with different phase offsets as well as single or multiple control acquisition.

Figure 8:
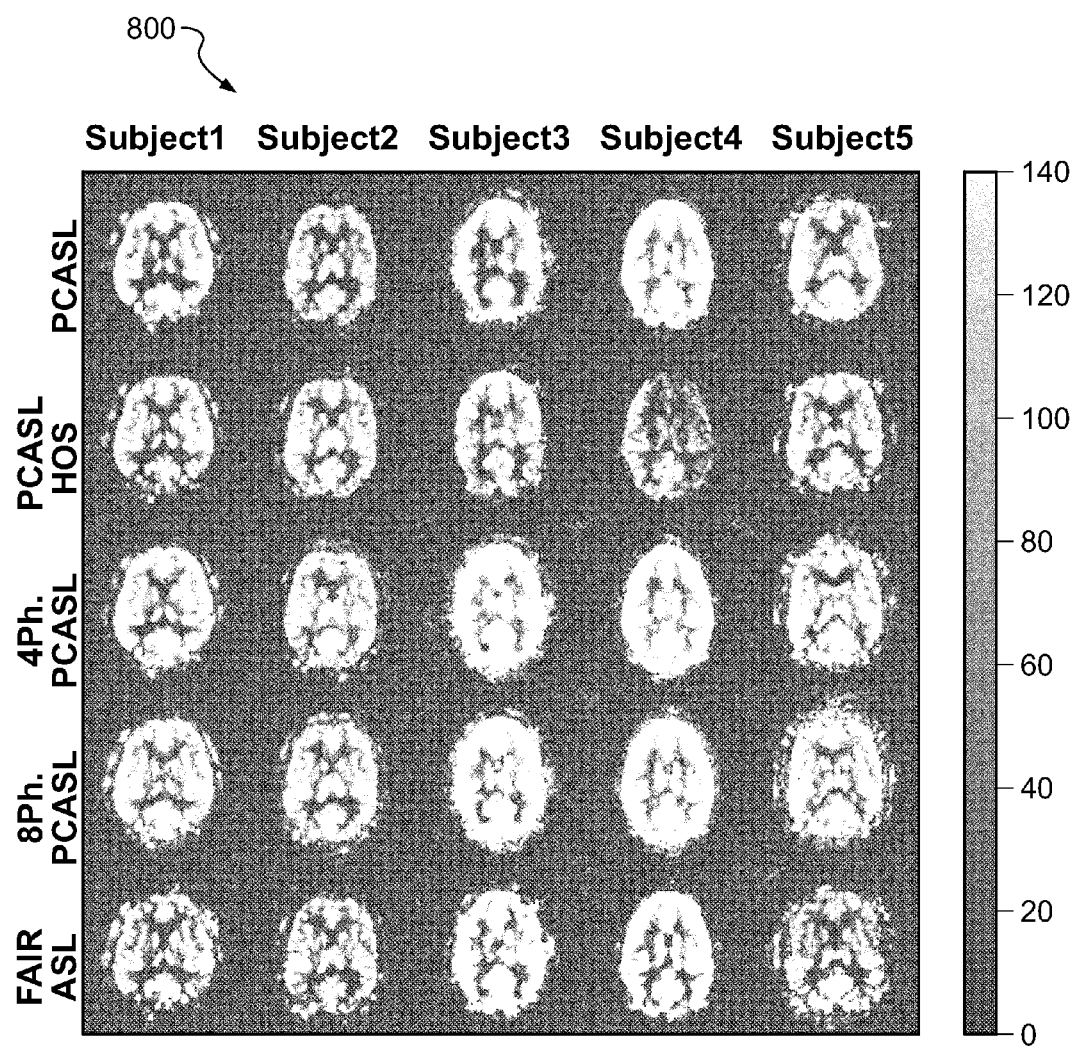
FIG. 8 shows single slice images acquired by different PCASL methods from all 5 human subjects.

FIG. 8 shows single slice images 800 acquired by different PCASL methods from all 5 human subjects. The cerebral blood flow (CBF) maps of different PCASL methods over all 5 subjects. The physiological unit of images is ml/100 tissue/min. The CBF maps acquired with the proposed multi-phase PCASL (MP PCASL) method provides higher CBF estimates than conventional PCASL and PCASL with HOS when the tagging efficiency of the latter is reduced by phase errors.

Figure 9:
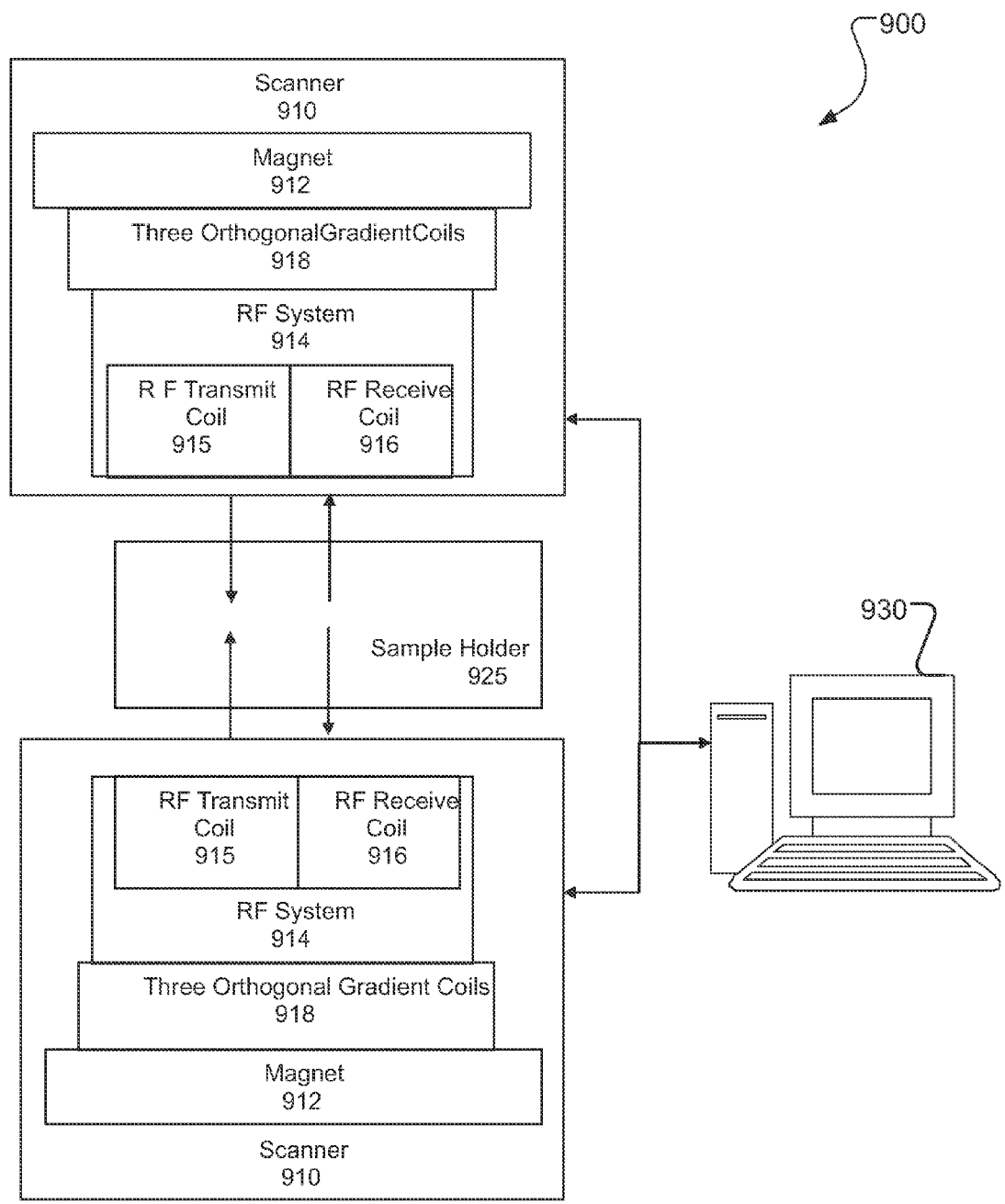
FIG. 9 shows an example MRI system.

FIG. 9 shows an example MRI system 900 for performing MP PCASL. The MRI system 900 includes a scanner 910, a data processing apparatus 930 and a sample holder or table 925 for holding a sample. The scanner 910 can be implemented using any one of various MRI scanners including a 1.5 T Sigma TwinSpeed scanner and a 3T Sigma TwinSpeed scanner (available from GE Healthcare Technologies, Milwaukee, Wis.) The scanner 910 includes a main magnet 912, three orthogonal gradient coils 918 and a RF system 914. The main magnet 912 is designed to provide a constant, homogeneous magnetic field. The three orthogonal gradient coils 918 are designed to provide three orthogonal, controller magnetic gradients used to acquire image data of a desired slice by generating an encoded and slice-selective magnetic field. The RF system 914 includes a RF transmit coil 915 and a RF receive coil 916 designed to transmit and receive RF pulses. The RF system 914 can further include a RF synthesizer (not shown) and a power amplifier (not shown). In some implementations, an integrated transceiver coil (not shown) can be implemented instead of the separate transmit coil 915 and receive coil 916 for transmitting and receiving RF signals. For example, a close-fitting smaller coil can improve image quality when a small region is being imaged. Further, various types of coils that are placed around specific parts of a body (e.g., the head, knee, wrist, etc.) or even internally can be implemented depending on the sample and imaging applications.

The MRI system 900 is designed to perform the techniques disclosed in this specification. In particular, the MRI system 900 is designed to implement the methods disclosed with respect to FIG. 7. The RF system 914 is designed to apply to a target subject a non-selective inversion RF pulse, a slice-selective inversion RF pulse and a half RF excitation pulse. The three orthogonal coils 918 are designed to apply slice-selective magnetic field gradients (of a first polarity and a second polarity) and magnetic readout gradients. The data processing apparatus (e.g., a computer) 930 is designed to receive and process the acquired data to obtain desired images corresponding to the short T2 components.

The pseudo-continuous arterial spin labeling (PCASL) method for CBF quantification offers higher SNR and therefore the potential for improved quantification compared to pulsed ASL (PASL). In addition, it can be implemented without the need for a special RF system, which is often required for continuous ASL (CASL). However, because the tagging mechanism is highly sensitive to the accurate specification of phase between successive RF pulses, the tagging efficiency of PCASL can be significantly modulated by both gradient imperfections and the presence of off-resonance fields at the tagged vessels. In another aspect, PCASL techniques and systems are described with multiple phase offsets which are less sensitive to these factors. The PCASL techniques and systems as described provide more robust CBF values than the conventional PCASL method and higher SNR than FAIR ASL, a commonly used pulsed ASL method.

Conventional ASL has two phases in its acquisition (tag and control). For PCASL, the tag and control phases are defined by the phase increment between two successive RF pulses. The overall phase increment between two successive RF pulses can be expressed by an equation: $\Delta\theta n = \gamma G t d + 2\pi n/N$, where γ is the gyromagnetic ratio, G is the average gradient strength, t is the interval between RF pulses, d is the distance from the gradient center to tagging location, n denotes the nth phase, and N is the number of phases. Here γGtd is the phase tracking term and 2πn/N is the phase offset which generates different amounts of inversion. FIG. 3 shows the inversion response as a function of the phase offset. Conventional PCASL method uses two phase offsets: 0° for tag and 180° for control. When the predefined tracking phase has errors due to off-resonance and gradient imperfections, the desired tagging efficiency may not be achieved. For example, if there is a 90° phase offset, the tagging efficiency becomes zero. Acquiring multiple phases with evenly distributed phase offset (shown in FIG. 3 as □ for 4 phases and × for 8 phases) reduces sensitivity to the phase errors because it allows the acquired data to be fit to a predefined inversion response function. This enables the estimation of the perfusion signal on a per-voxel basis. From the fitting algorithm the phase tracking errors can also be estimated.

Figures 10A, 10B, 10C:
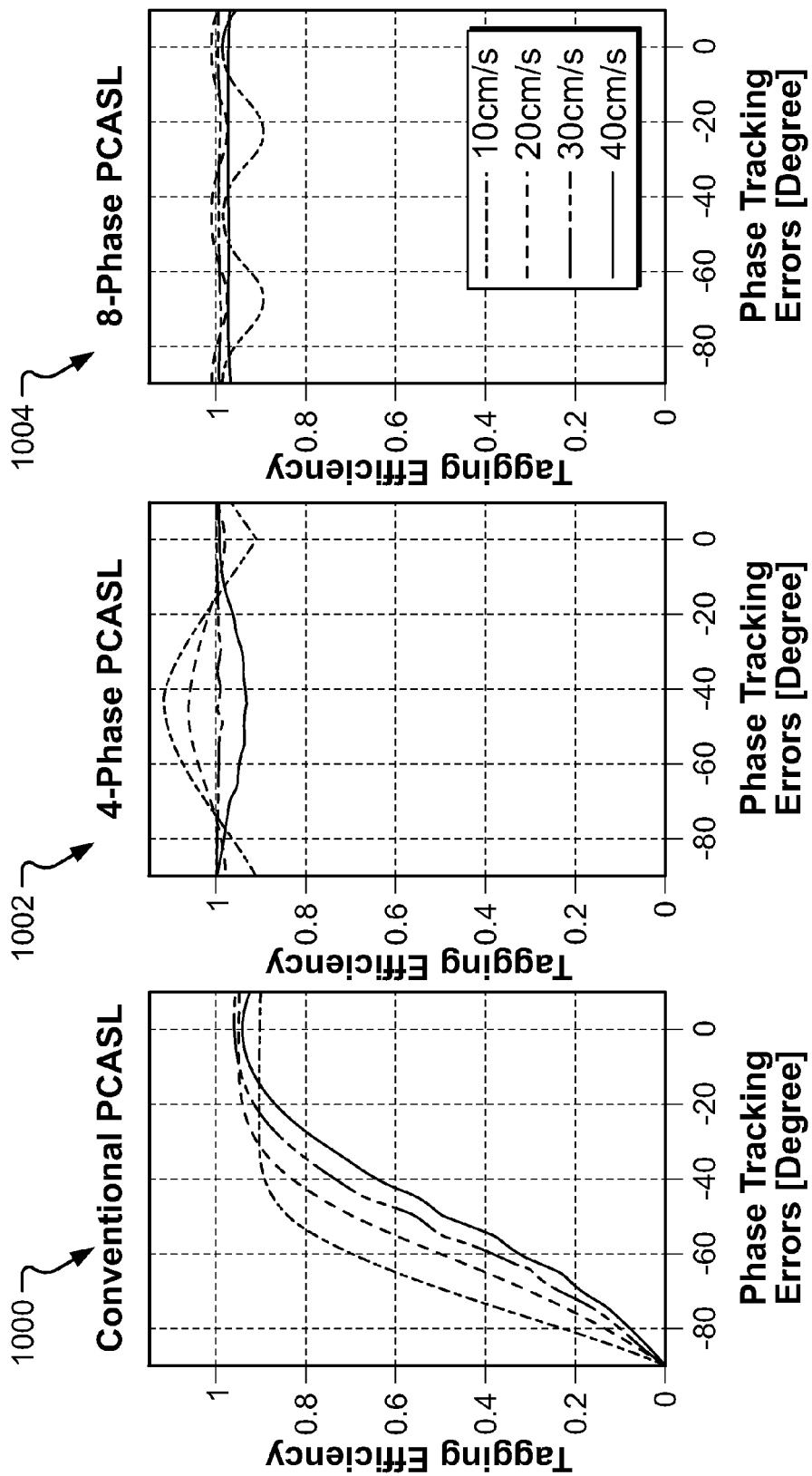
FIGS. 10a, 10b, and 10c are data diagrams that show tagging efficiencies corresponding to arterial velocities and phase tracking errors.

FIGS. 10a, 10b, and 10c are data diagrams 1000, 1002 and 1004 that show tagging efficiencies corresponding to arterial velocities and phase tracking errors. As reported in previous publications (8, 10, 11), the tagging efficiency of conventional PCASL is sensitive to arterial velocities (FIG. 10a). The estimated magnetization with multi-phase PCASL (FIGS. 10b and 10c) are also sensitive to phase tracking errors especially at the velocity of 10 cm/s but the variability is much lower in MP-PCASL than conventional PCASL. 8-phase PCASL shows lower sensitivity to arterial velocities and phase tracking errors than 4-phase PCASL. For 4-phase PCASL, overestimation of magnetization due to errors in the fitting procedure causes tagging efficiencies higher than one at lower velocities than an assumed velocity of 30 cm/s (FIG. 10b).

Figure 11B:
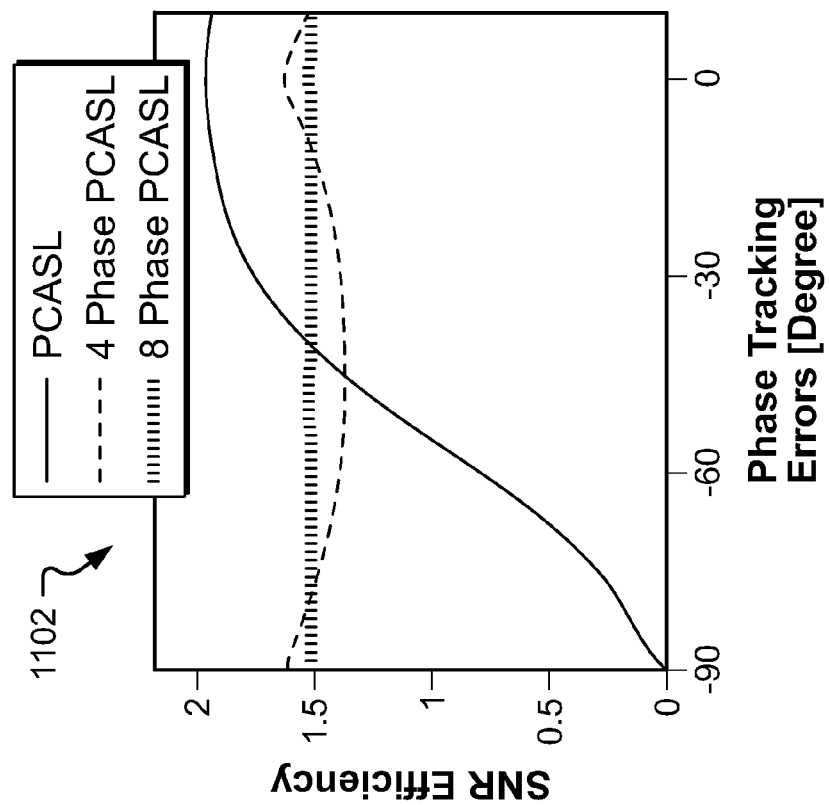
FIGS. 11a and 11b show Monte-Carlo simulation result of estimated ASL signal and SNR efficiency.
Figure 11A:
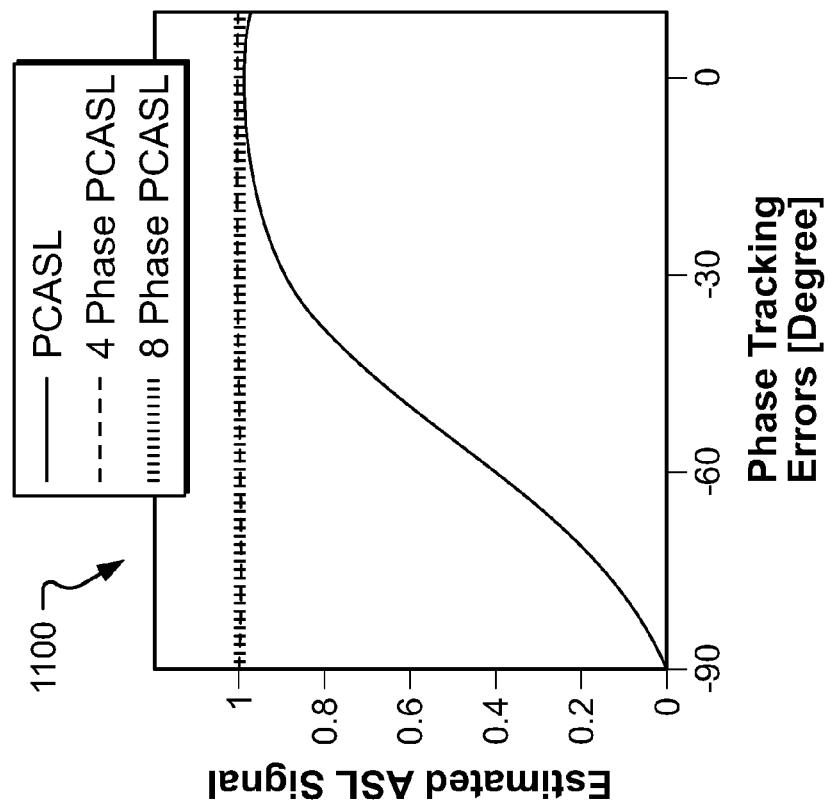

Monte-Carlo simulation can be performed to estimate the ASL signal and examine the SNR efficiency (SNR in unit of scan time normalized to that of pulsed ASL) as a function of phase offset. FIGS. 11a and 11b are diagrams 1100 and 1102 that show the result of the simulation. In the simulation, the MP PCASL method provides consistent estimation of the ideal ASL signal and no significant loss of SNR. (SNR loss of 22.4%). The CBF values are compared from 4 different ASL methods over 5 subjects (3 men and 2 women): FAIR ASL, PCASL with high order shimming, and 4 and 8 phase PCASL. The experiment can be executed on a MRI system (e.g., MRI system 900), such as a 3T Signa HDx scanner with an 8-channel head coil (GE Healthcare, Waukesha, Wis.). The FAIR ASL scan is performed with QUIPSS II post-inversion saturation pulses and scan parameters are TI1/TI2=600 ms/1600 ms, 10 cm tag width, 3 cm tag-slice gap TR 2.6 sec, 112 reps. PCASL scan parameters are 1600 msec tag duration, 1000 ms post labeling delay, TR 3.6 sec, 80 reps. All methods have 240 mm FOV, 20 slices (5 mm thick, skip 1 mm), single-shot spiral acquisition (TE=3 ms), and 5 min. scan time. A mean gray matter CBF values are obtained from the gray matter mask which was defined with a high resolution anatomical scan.

Figure 12:
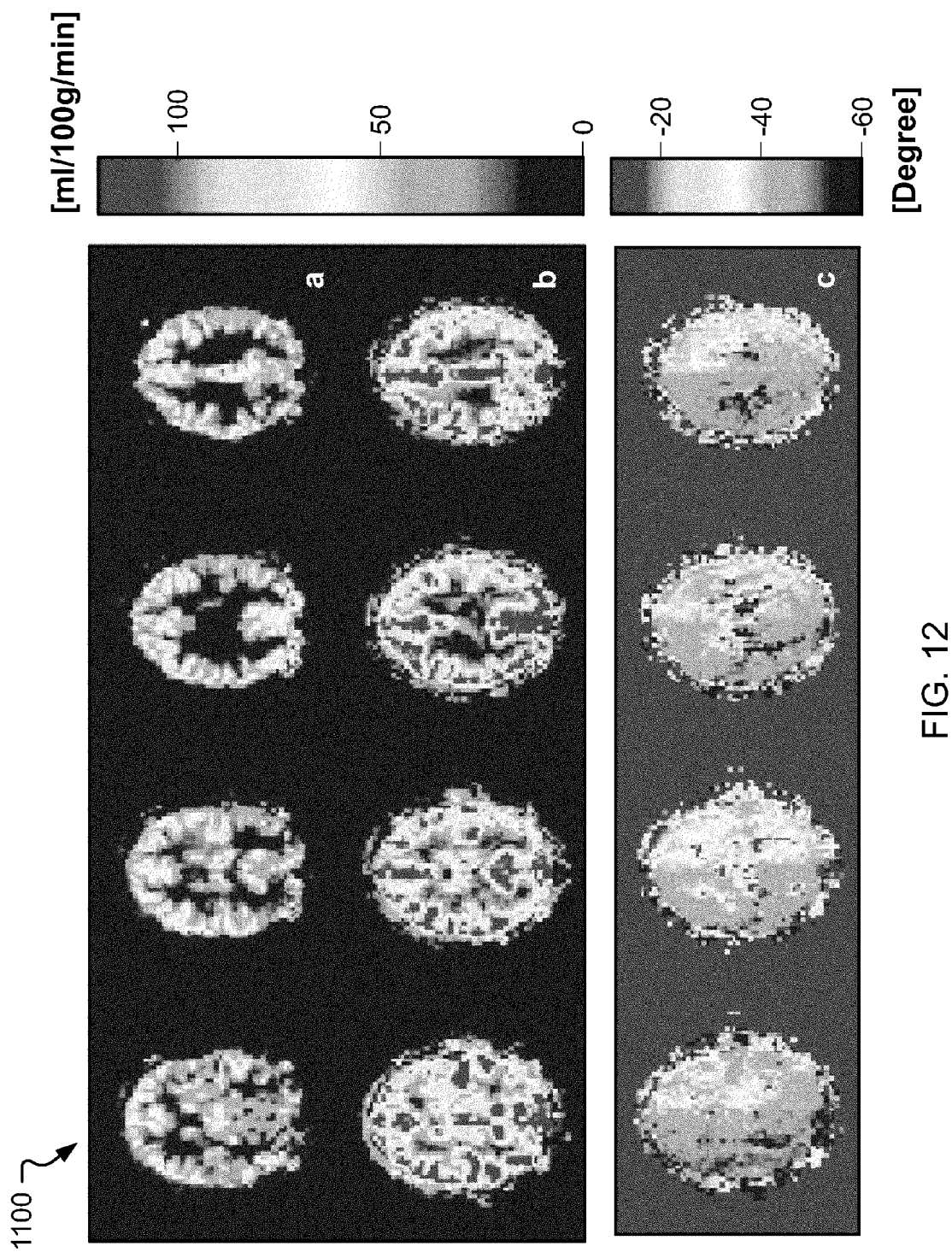
FIG. 12 show CBF maps from PCASL and 4-phase PCASL.

As shown in FIG. 12, panels a, b and c, the CBF maps acquired with the proposed multi-phase PCASL (MP PCASL) method provides higher CBF estimates than conventional PCASL when the tagging efficiency of the latter is reduced by phase errors. In addition to the ASL signal, the fitting algorithm provides estimates of the phase tracking errors on a per-voxel basis. These errors should be uniform across each vascular territory, providing additional opportunities for robust estimation (panel c).

Figure 13:
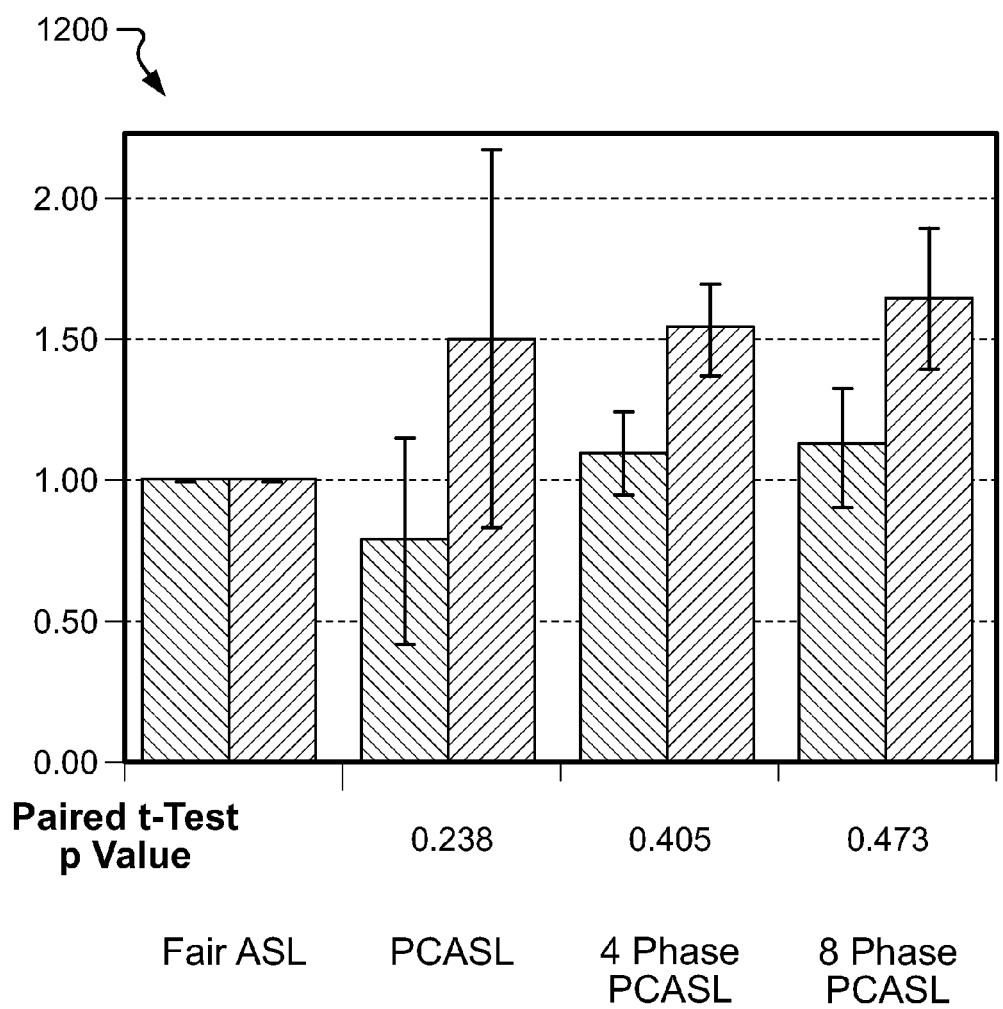
FIG. 13 shows comparisons of gray matter CBF (first bar of each pair) and SNR efficiency (second bar of each pair) normalized to the values from FAIR ASL.

FIG. 13 shows the mean gray matter CBF values and SNR efficiency (SNR per unit of scan time) normalized to those from FAIR ASL images. The CBF measures obtained with the MP PCASL method are more consistent with the reference CBF values obtained with FAIR ASL as compared to those from conventional PCASL (see paired t-test p-values in FIG. 13). In addition, the smaller error bars in the normalized MP-CASL values indicates that the method is more robust than convention PCASL. There is not a significant difference between the mean gray matter CBF values acquired with the 4-phase and 8-phase PCASL methods (paired t-test p-value of 0.83). Both conventional PCASL and MP PCASL provide higher SNR than FAIR ASL method (second bars of each pair in FIG. 13).

CBF estimation based on a fitting algorithm with parameters fit at 30 cm/s arterial velocity can be sensitive to arterial velocity. For higher number of phases, such as 8 phases, representative voxels can be used for selecting an optimum fitting curve to reduce sensitivity to different arterial velocities. Using representative voxels, multiple combinations of values can be tested and the values that produce minimum fitting errors are selected to tailor a fitting curve applied to all other voxels. For example, a simulation can be performed to examine the tagging efficiency sensitivities of 8-phase PCASL with a fixed fitting curve (e.g., $\alpha=54\beta=13$) and a tailored fitting curve across the arterial velocity range of 10 to 50 cm/s and the phase tracking error range of −90 to 10 degrees. The inversion response curves obtained from the Bloch were utilized for this simulation. The tagging efficiency can be calculated by taking the ratio of the estimated magnetization with the fitting procedure to the fully relaxed magnetization of arterial blood. The results are shown in FIGS. 14a and 14b.

Figure 14A:
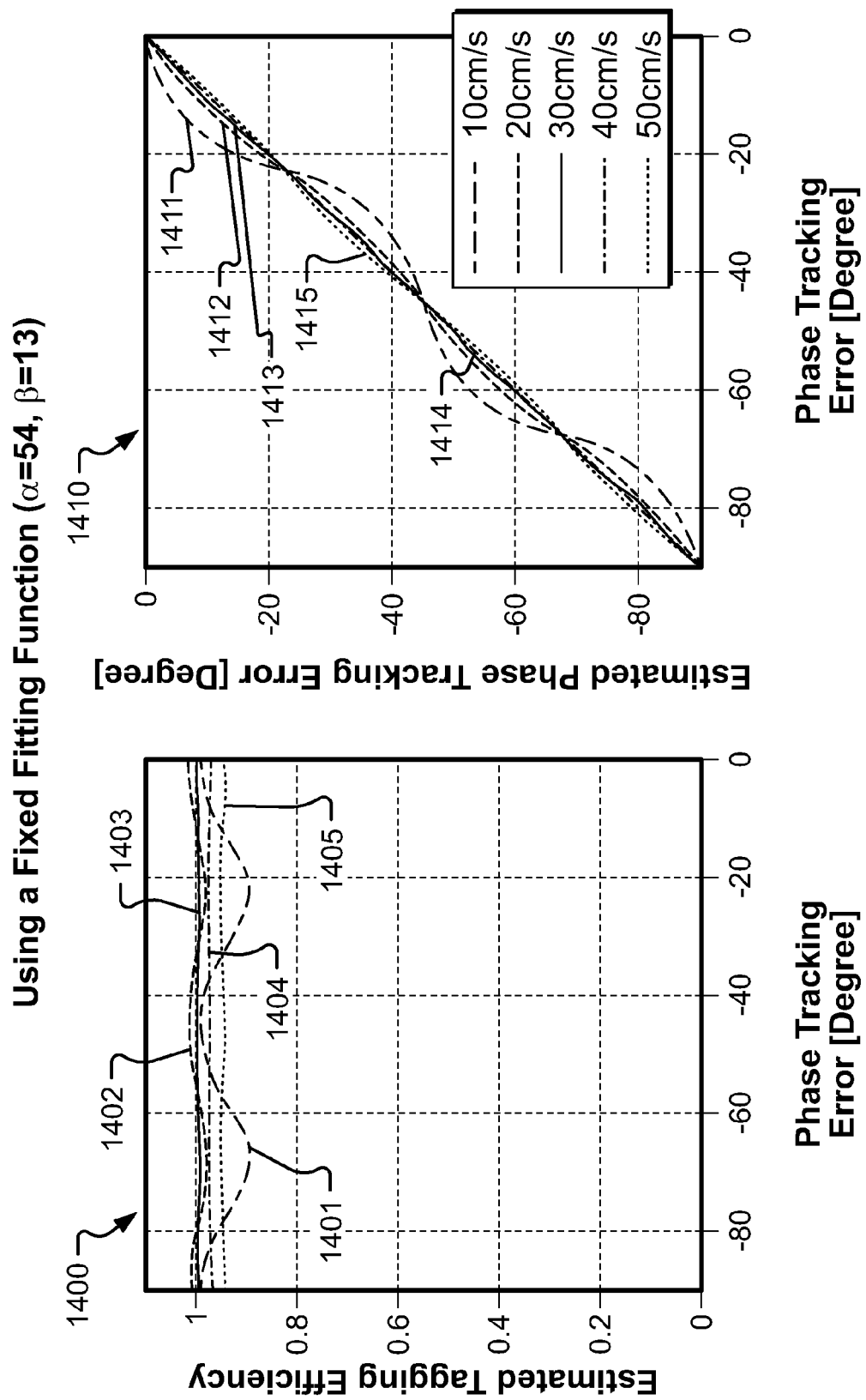
FIG. 14a shows estimated tagging efficiencies and phase tracking errors to various arterial velocities and phase tracking errors using a fixed fitting function.
Figure 14B:
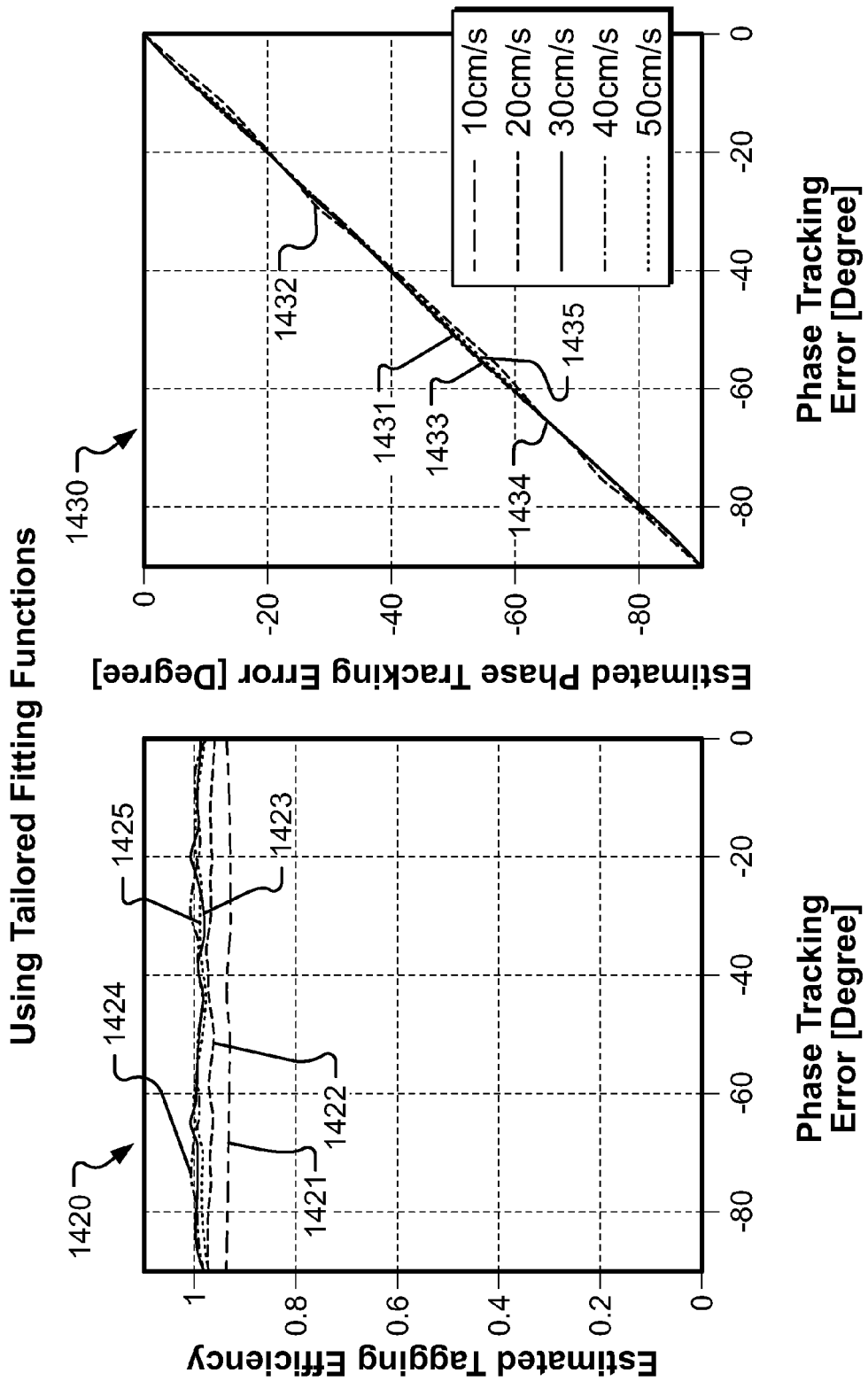
FIG. 14b represents those values using the tailored fitting function to each velocity and phase tracking error.

FIG. 14a includes data charts 1400 and 1410 that show the estimated tagging efficiencies and phase tracking errors to various arterial velocities and phase tracking errors using a fixed fitting function. FIG. 14b includes data charts 1420 and 1430 that represent those values using the tailored fitting function to each velocity and phase tracking error. The proposed algorithm can provide robust and accurate estimations of CBF and phase tracking errors. Reference numbers 1401, 1411, 1421 and 1431 represent various data with respect to an arterial velocity of 10 cm/s; reference numbers 1402, 1412, 1422 and 1432 represent various data with respect to an arterial velocity of 20 cm/s; reference numbers 1403, 1413, 1423 and 1433 represent various data with respect to an arterial velocity of 30 cm/s; reference numbers 1404, 1414, 1424 and 1434 represent various data with respect to an arterial velocity of 40 cm/s; and reference numbers 1405, 1415, 1425 and 1435 represent various data with respect to an arterial velocity of 50 cm/s.

In another aspect, arterial spin labeling (ASL) fMRI can provide quantitative measurements of functional changes in cerebral blood flow (CBF) that can be used either on their own or in conjunction with BOLD measures. The continuous arterial spin labeling (CASL) or the pseudo-continuous arterial spin labeling (PCASL) method offers higher SNR and therefore the potential for improved detection of activation compared to pulsed ASL (PASL). However, a prior study has reported differences in the functional CBF activation measured by CASL versus PASL. PCASL can be implemented without the need for a special RF system, which is often required for continuous ASL (CASL). The quantification of CBF activation with PCASL has not yet been examined in detail, and may be sensitive to phase errors. The PCASL method is optimized by estimating and compensating the phase errors at the tagging vessels. Our result shows good agreement in quantitative CBF measures between PICORE ASL (a PASL method) and our optimized PCASL method.

Figure 15:
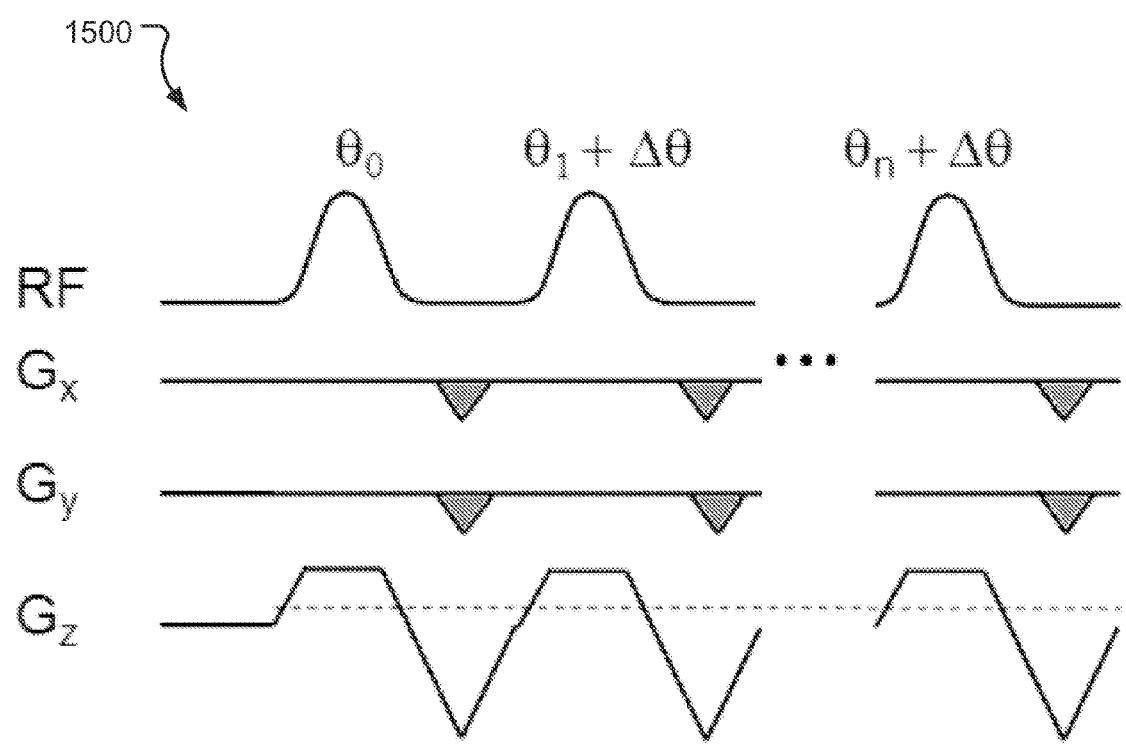
FIG. 15 shows a diagram of tagging modulation with the additional phase offset ($\Delta\theta$) and compensation gradients expressed by the shaded area in Gx and Gy.

FIG. 15 shows a diagram of tagging modulation with the additional phase offset ($\Delta\theta$) and compensation gradients expressed by the shaded area in Gx and Gy. The tagging efficiency of PCASL can be significantly modulated by both gradient imperfections and the presence of off-resonance fields at the tagged vessels because the tagging mechanism is highly sensitive to the accurate specification of phase between successive RF pulses. The conventional PCASL method uses two phase offsets: 0° for tag and 180° for control. The phase errors can be estimated between RF pulses using a novel PCASL method with multiple phase offsets (i.e. −90°, 0°, 90°, 180°) which is less sensitive to those factors because it, allows the acquired data to be fitted to a predefined inversion response function. This enables the estimation of the phase errors as well as the perfusion signal on a per-voxel basis. The estimated phase error which is global through a tagging plane can then be compensated by adding a constant phase offset to the labeling RF pulses ($\Delta\theta$ in FIG. 15). However, the labeling plane typically contains several blood vessels, each of which may have a different phase error due to the local field frequency offset, causing non-uniform tagging efficiency across blood vessels. This asymmetric tagging efficiency can be compensated by adding gradients in x and y plane (shaded gradient area in FIG. 15). A uniform and near-optimal tagging efficiency across all tagged vessels can be achievable.

Figure 16:
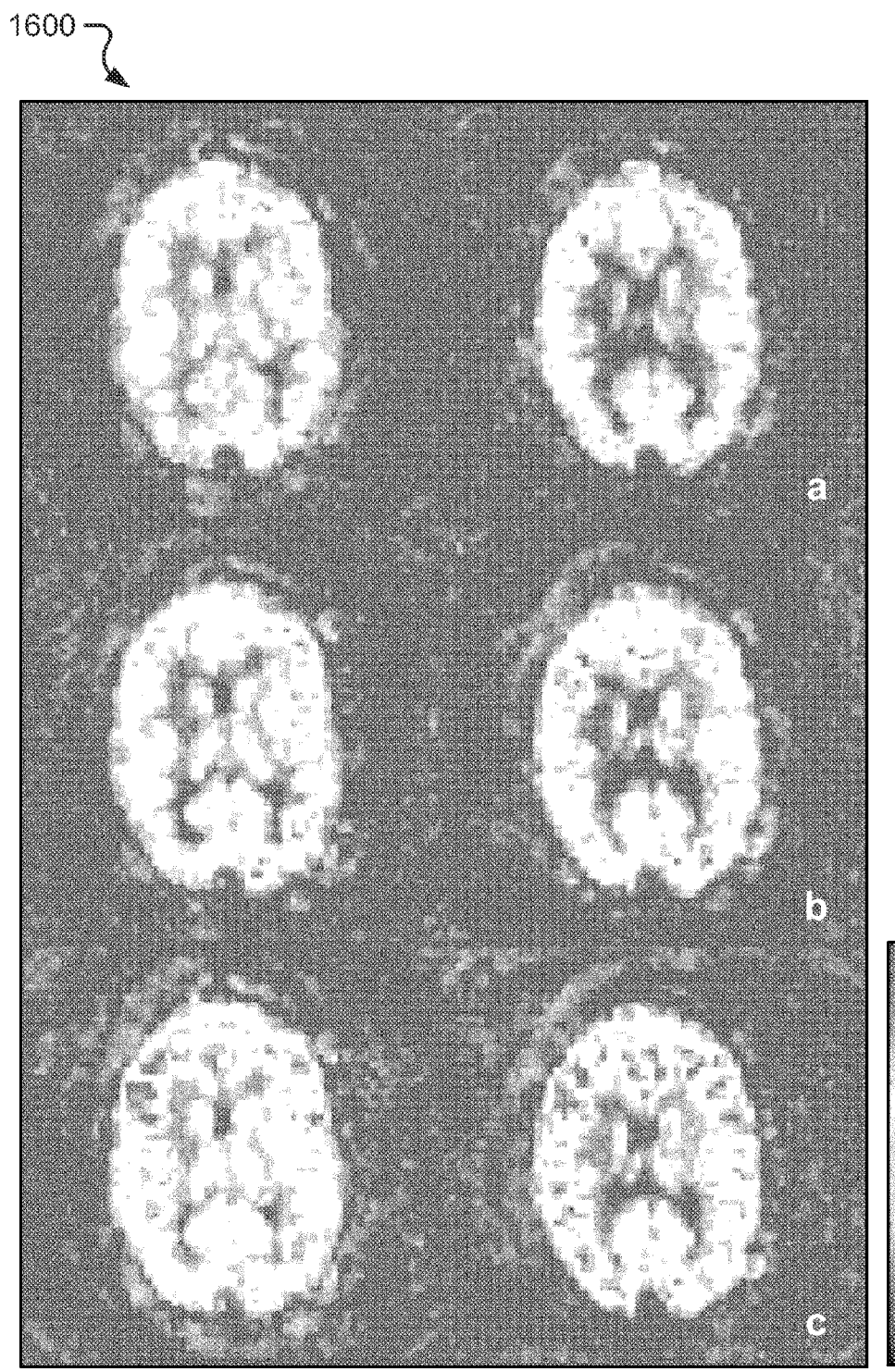
FIG. 16 shows tSNR maps from (a) PICORE ASL, (b) PCASL, and (c) the optimized PCASL.

The visual activation is compared in one female subject across 3 different ASL methods: PICORE ASL, PCASL, and the optimized PCASL. FIG. 16 shows tSNR maps from (a) PICORE ASL, (b) PCASL, and (c) the optimized PCASL. The experiment can be executed on a MRI system (e.g., MRI system 900), such as a 3T Signa HDx scanner with an 8-channel head coil (GE Healthcare, Waukesha, Wis.). The PICORE ASL scan is performed with QUIPSS II post-inversion saturation pulses and scan parameters were TI1/TI2=600 ms/1900 ms, 10 cm tag width, 1 cm tag-slice gap, TR 2 sec. PCASL scan parameters are 1600 msec tag duration, 1200 ms post labeling delay, 5 cm tag-slice gap TR 3 sec. All methods have 240 mm FOV, 6 slices (5 mm thick, no gap), single-shot spiral acquisition (TE=3 ms). Each method includes two scans: one scan to measure baseline CBF (3 min) and a block design scans (30 s off, 4 cycles of 30 s on/30 s off; 8-Hz flickering checkerboard visual stimulus). All the CBF data are calibrated to physiological units of (ml/100 g/min).

Figure 17:
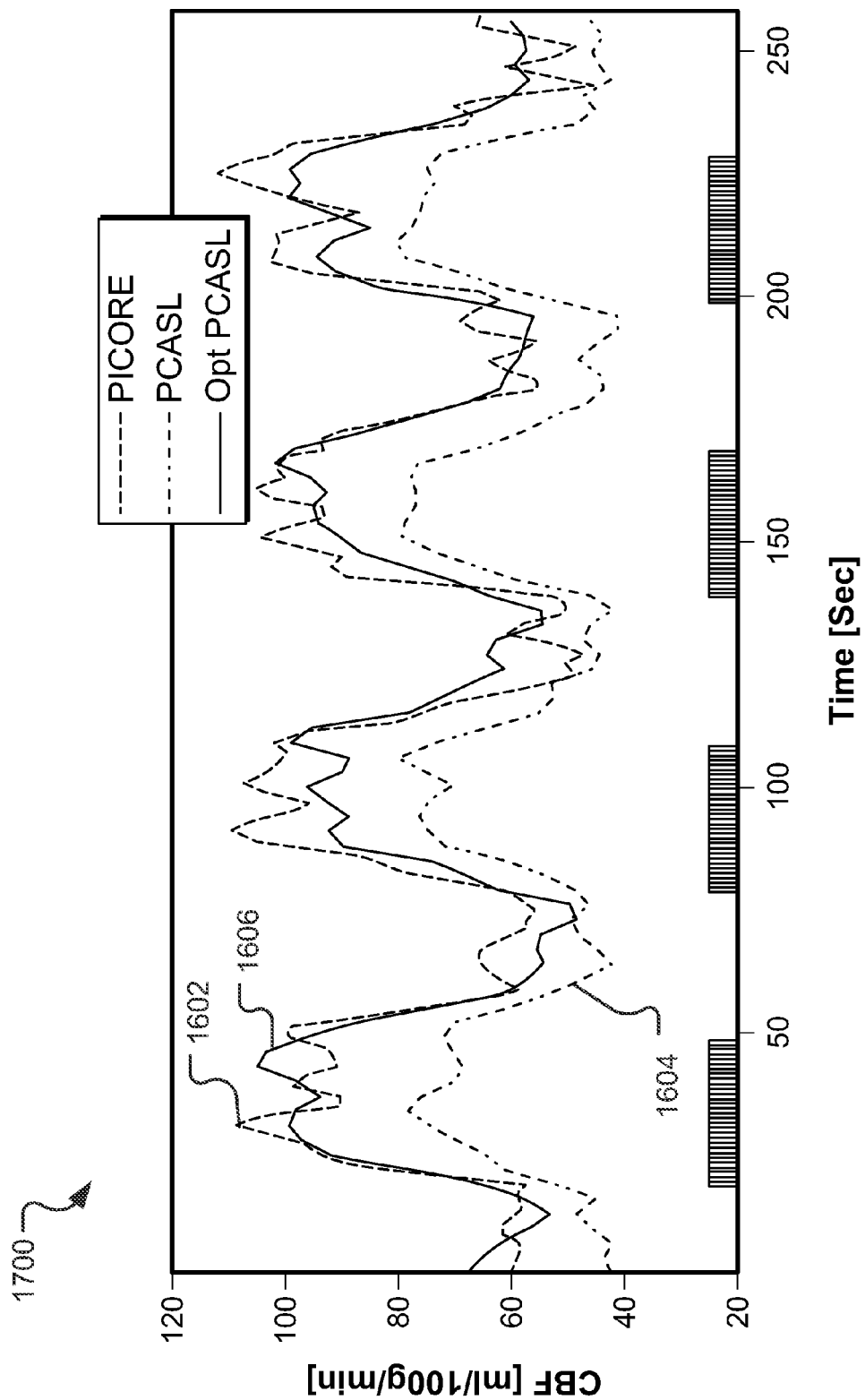
FIG. 17 shows averaged time courses from the common activated ROI (total 89 voxels) expressed in the physiological unit of perfusion.

FIG. 17 shows averaged time courses from the common activated ROI (total 89 voxels) expressed in the physiological unit of perfusion. As shown in FIG. 17, both the PCASL and the optimized PCASL provide higher tSNR (mean divided by standard deviation over time) than PICORE ASL method but PCASL gave lower tSNR than optimized PCASL due to the non-optimal tagging efficiency. The time course in quantified CBF unit (ml/100 g/min) shows there was good agreement in quantitative CBF measures between PICORE and PCASL. FIG. 18 is a table that shows baseline CBF (CBF0) and the changes of CBF (ΔCBF) from three ASL fMRI methods. The change in CBF from the optimized PCASL method is comparable to that from the PICORE ASL method. The compensation or correction of the phase errors at tagging plane in PCASL acquisition is essential for higher SNR and accurate CBF quantification.

FIGS. 19a and 19b show relative mean gray matter CBF values 1900 and SNR efficiencies 1910 normalized to those from the FAIR ASL method and measured phase tracking errors over different vascular territories. For the average of mean gray matter CBF in FIG. 19a, the difference between the estimates obtained with the two MP-PCASL methods was 1.8% whereas estimates with conventional PCASL and PCASL with HOS were 23% and 47% lower, respectively, than the MP-PCASL estimates. Estimates obtained with 4 Phase PCASL and 8 Phase PCASL were not significantly different (paired t-test: p>0.64) to those obtained with FAIR ASL. All PCASL methods provided higher SNR than FAIR ASL method (FIG. 19b). The SNR efficiencies of 4-phase and 8-phase PCASL were 51% and 65% higher than that of FAIR ASL method, respectively. FIGS. 19c and 19d show the measured phase tracking errors 1920 and tagging efficiency losses 1930 in conventional PCASL in three vascular territories, respectively. The measured phase tracking errors ranged from −25 to −50 degrees across subjects and vascular territories. Within subjects the measured tagging efficiency losses across vascular territories tended to show similar variability to the phase tracking errors. The mean tagging efficiency loss in conventional PCASL was 23% and it is consistent with the results of previous studies, which reported tagging efficiency losses of 20% in Wu et. al. (11), 19% in Dai et. al. (10), and 25% in Pohmann et. al (26). A scatter plot 1940 of the tagging efficiency losses to the phase tracking errors is shown FIG. 19e. Positive correlation between the tagging losses and the phase tracking errors was observed across subjects and vascular territories and the results showed an overall agreement with the simulations. The subject variability of arterial velocities may explain the wide spread of the tagging losses in FIG. 19d compare to the phase tracking errors in FIG. 19c.

The three main challenges of measuring white matter perfusion using ASL MRI are: low SNR, partial volume, and transit time effects. The described optimized PCASL method has sufficient SNR to detect perfusion in major white matter tracks. The adverse effects of partial volume can be limited by carefully selecting voxels containing mostly white matter. Results indicate significant variability of the white matter transit time across brain regions. Therefore it may be recommended that separate ASL experiments are carried out with parameters tailored to the specific targeted white matter regions to ensure optimal signal and accurate measurements.

The CBF values obtained with the proposed MP-PCASL methods were higher than those of conventional PCASL and were more consistent with the measures obtained with FAIR. At the same time, MP-PCASL retained much of the SNR advantage of conventional PCASL. Because of these properties, the MP-PCASL method would be advantageous in clinical applications of ASL that require robust and accurate quantitative measures of CBF.

For MP-PCASL, the relative mean GM CBF values normalized to the values from FAIR ASL in FIG. 19a showed a level of variability that is greater than would be expected from reproducibility of CBF measurements (~10%) between runs within a scan session. For example, subject 1's 8-phase PCASL CBF value is approximately 25% higher than the FAIR ASL value, while subject 4's 8-phase PCASL value is about 10% lower than the FAIR ASL value. Possible factors for this variability are transit delay effects and differences in tagging efficiency. Because the tagging duration of PCASL (1.6 s) was longer than the QUI PSS II time of FAIR ASL (0.6 s), PCASL is less sensitive to transit delays. For subjects with longer transit delays, the CBF values obtained with FAIR ASL will tend to be biased low as compared to the PCASL values. As shown in diagrams 2000, 2010, 2020 and 2030 of FIGS. 20a, 20b, and 20c, MP-PCASL effective tagging efficiencies can be modulated by the arterial velocities. For FAIR ASL, the tagging efficiency can be modulated by $B_1$ field inhomogeneity especially at the distal tagging area (close to the neck) when the $B_1$ field may be reduced by more than 30%. Therefore, deviations of the actual tagging efficiency from the assumed efficiency can also lead to mismatches between the CBF values obtained with FAIR ASL and MP-PCASL.

Because FIG. 19c showed that measured phase tracking errors were fairly consistent across subjects except Subject 3, implementing a uniform compensation of the error (−30 degrees) in the RF schedules of conventional PCASL could represent a simple solution that would reduce tagging efficiency losses. However, this is not likely to be a generally optimal solution since the variability across subjects and vascular territories is sensitive to arterial velocities as shown in FIG. 19e and may be greater in certain clinical populations, such as older patients with vascular disorders. In addition, variations across multiple scan sessions and different sites should be also considered for longitudinal or multi-site studies since off-resonance fields depends on the shimming profiles of each scan and scanners at different sites are likely to exhibit differences in shimming and gradient performance.

Although the MP-PCASL method can provide robust perfusion estimation, it may not be a suitable method for applications that require higher temporal resolution CBF measures, such as fMRI, because the temporal resolution is decreased by the need to acquire additional phases. In addition to lower temporal resolution, the SNR of the MP-PCASL method is lower than that of the conventional PCASL when the phase tracking error is small. Therefore, correcting the phase tracking errors in conventional PCASL will be especially beneficial for applications in which maximal SNR is desired and time is available for tuning the acquisition to correct for the errors. In these cases, the MP-PCASL method may be used to estimate the phase tracking errors since the fitting algorithm enables the estimation of the errors as well as the perfusion signal on a per-voxel basis. Measures of phase tracking errors in a vascular territory will tend to reflect the errors at the corresponding feeding artery. For example, the errors in the left hemisphere can provide an estimate of the errors at the intersection of the tagging plane with the left internal carotid artery. This estimate can be utilized to set the proper tracking phase prior to a PCASL scan in order to obtain the optimum SNR. This optimization method would also be beneficial to applications which require multiple ASL acquisitions, such as vessel-encoded ASL and transit delay measurement.

The tagging scheme with zero-mean gradient control is reported to be less sensitive to the off-resonance effects at the tagging location. However, based on our simulation the off-resonance sensitivity of both methods is similar when the phase tracking error is smaller than π/2 (see FIG. 20c). Although we have presented the concept of multi-phase acquisition with the nonzero-mean gradient control scheme, the method is equally applicable to the zero-mean gradient control scheme.

In another aspect, measuring white matter perfusion using arterial spin labeling (ASL) MRI is challenging for various reasons: perfusion in white matter is low compared to that in gray matter, resulting in a lower intrinsic signal to noise ratio (SNR); the relative low resolution of ASL MRI images causes partial volume effects and overestimation of white matter perfusion due to contamination from the neighboring gray matter; finally, the wide spread of transit time across white matter regions introduces bias in the perfusion measurements. Previous attempts in measuring white matter perfusion have used both pulsed ASL and continuous ASL. Despite having the advantage of higher SNR over pulsed ASL, continuous ASL suffers from low tagging efficiency which partially cancels its SNR advantage. An optimized pseudo-continuous ASL (PCASL) method is described that greatly improves the tag efficiency (see Theory section). The techniques and systems described in this specification allow utilization of the SNR gain of this optimized PCASL method in measuring the transit time and perfusion in major white matter regions across the brain.

The tagging efficiency of PCASL is impaired by phase errors due to both gradient imperfections and local field frequency offset at the labeling plane. Conventional PCASL uses two constant RF phase offsets (0° and 180°) to alternate between tag and control conditions assuming zero phase errors. Instead the phase errors can be estimated by acquiring MRI signal at multiple phase offsets (i.e. −90°, 0°, 90°, 180°) and fitting the data to a signal equation describing the PCASL labeling process. The estimated phase error can then be compensated by adding a constant phase offset to the labeling RF pulses. However, the labeling plane typically contains several blood vessels, each of which may have a different phase error due to the local field inhomogeneities, causing non-uniform tagging across blood vessels. This can be addressed by adding small XY shim gradients during labeling period whose amplitudes are determined by the magnetic field difference between the vessels. Therefore, by properly compensating for the phase errors, uniform and optimal tagging efficiency can be achieved in PCASL.

A healthy human subject is studied. All data are acquired on a MRI system (e.g., MRI system 900), such as a General Electric (GE) Signa HDx 3.0 Tesla research scanner with a standard 8 channel head coil (GE, Milwaukee, Wis.). The labeling plane is placed in a relatively straight part of the internal carotid artery approximately 30 mm inferior to the bottom slice as guided by a quick angiography scan. The perfusion scans are done using an in-house PCASL pulse sequence with single shot spiral acquisition. The scan parameters are: TR 5 s, TE 3 ms, 22 slices, 4 mm thick with no gap, FOV 22 cm, 64×64 matrix, labeling duration 1.6 sec. Data with six different post-labeling delays {0.1, 0.5, 0.9, 1.3, 1.7, 2.5 sec} are acquired. Perfusion signals are calculated by surround subtraction of the tag-control series at each post-labeling delay. A field map is collected and used to correct the off resonance effect in the individual spiral images using an iterative approach. A diffusion tensor imaging (DTI) dataset with 25 directions, b value of 1000 s/mm², 64×64 matrix and echo planar readout is also acquired to assist in localizing major white matter tracts. Geometric distortions in the DTI data are corrected using the same field map. Additionally, a series of inversion recovery experiments with different recovery time are acquired in order to map the T1 values of white matter for accurate perfusion quantification. Finally a high resolution T1 weighted FSPGR (GE) dataset is collected and later segmented into partial volume maps of gray, white and CSF tissue types. The field map corrected perfusion data, DTI and T1 map data were motion corrected and registered to the FSPGR images. Transit time and mean perfusion are then estimated by fitting the measured perfusion signal to a single compartment perfusion model. Both voxel-based and region of interest (ROI) based curve fitting are performed. In order to minimize partial volume effects, the analysis is performed only in voxels with white matter partial volume>0.9 based on the white matter segmentation maps. The DTI fractional anisotropy (FA) and directional maps are used to guide the drawing of the white matter ROIs. A threshold of FA>0.4 is applied in selecting white matter ROIs in addition to the white matter partial volume threshold (0.9).

Figure 21:
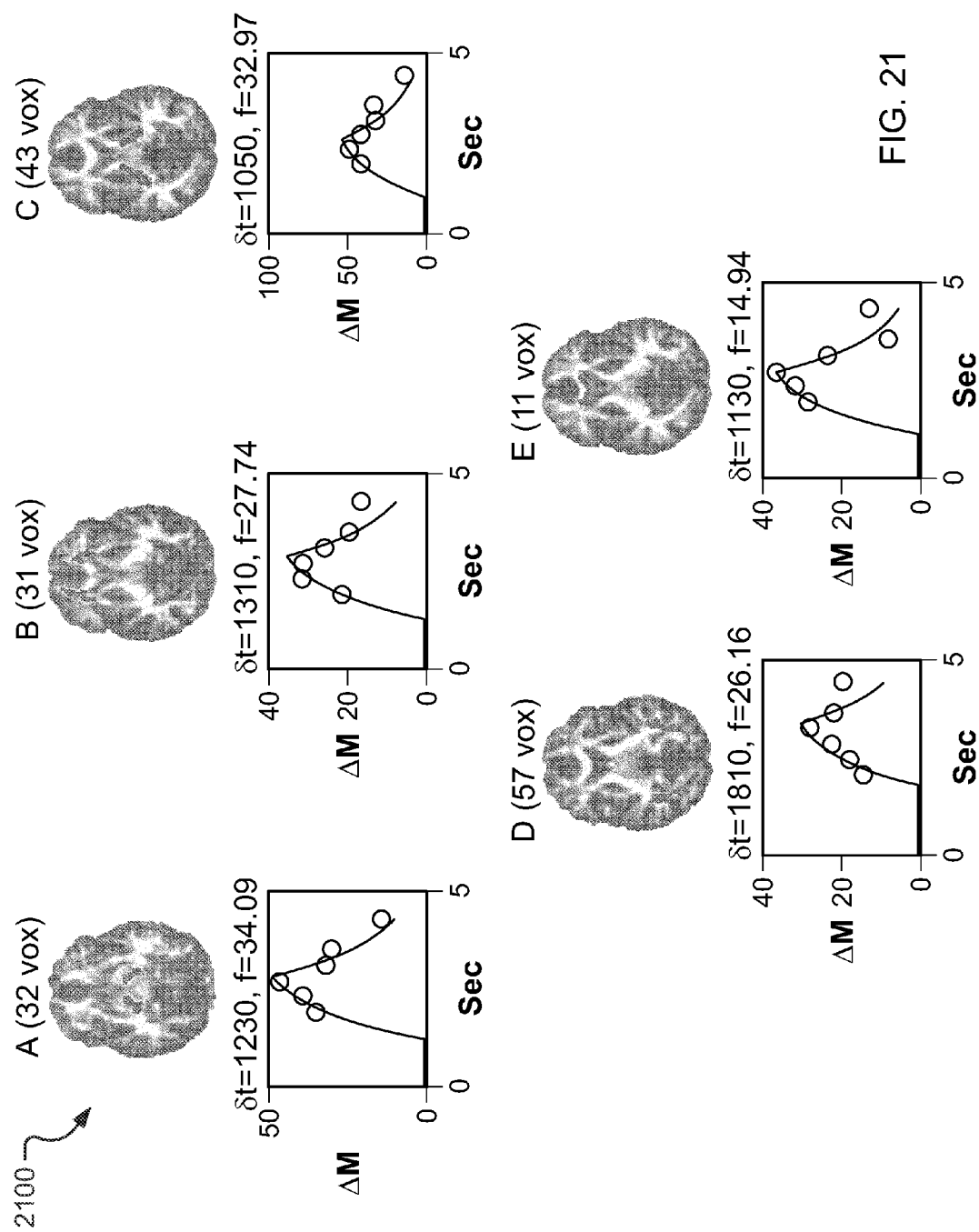
FIG. 21 shows (top row) the white matter ROIs overlaid on top of the fractional anisotropy maps and number of voxels contained in each ROI; and (bottom row) shows the ROI-based transit time curve fitting results. $\Delta$M is the raw perfusion signal, $\delta t$(msec) is the estimated transit time, and f(ml/100 g/min) is the quantified perfusion. (A. cortical spinal tract B. anterior portion of the inferior fronto-occipital fasciculus C. posterior limb of the internal capsule D. optic radiata E. genu of corpus callosum F. splenium of corpus callosum G. body of corpus callosum H. superior longitudinal fasciculus I. superior region of corona radiate.)
Figure 21:
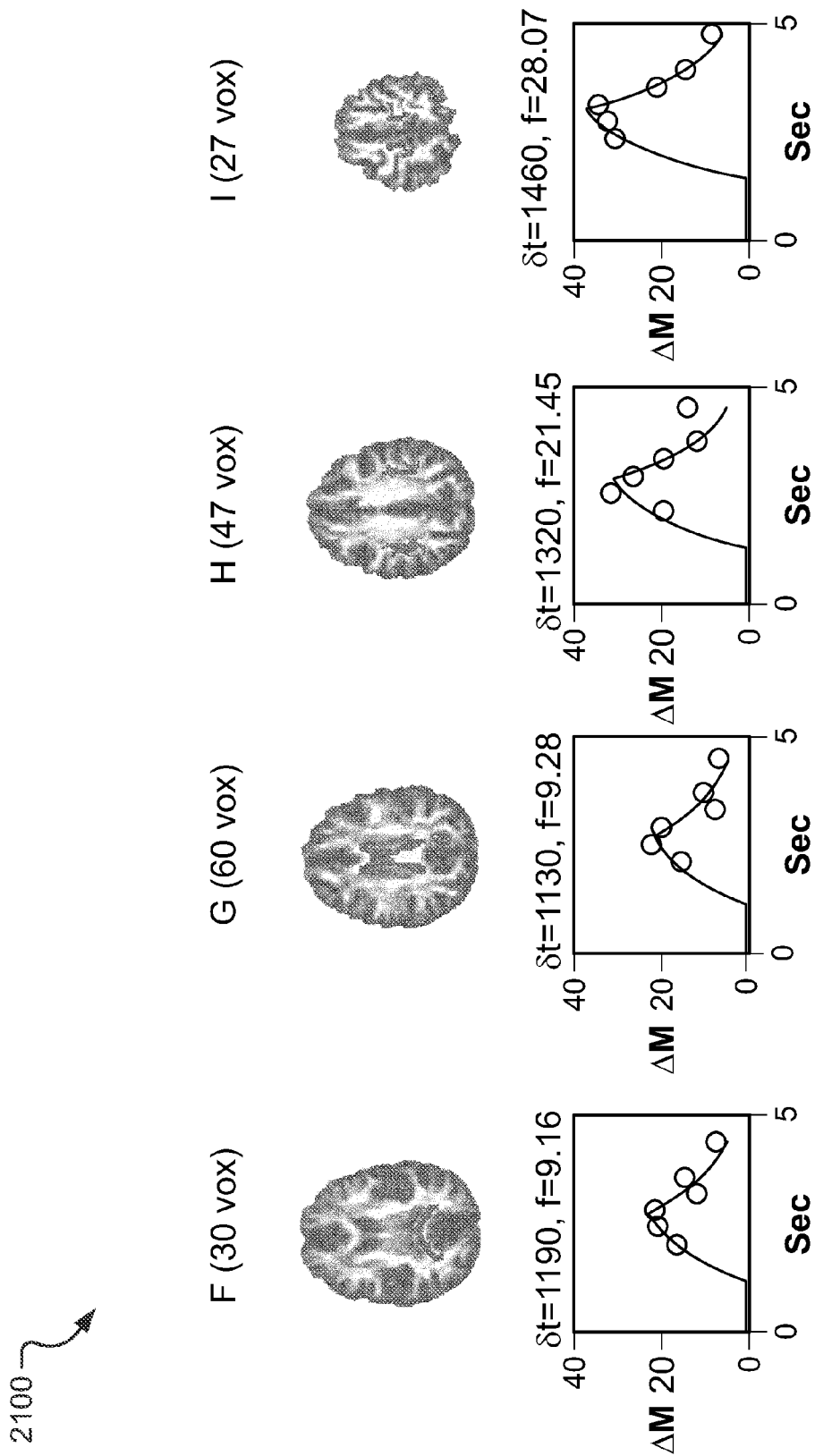

FIG. 21 shows the transit time fitting results 2100 in various white matter ROIs from the ROI-based analysis. The results indicated a wide spread of the white matter transit time (δt) and the perfusion values (f). The mean transit time and perfusion in whole brain white matter obtained from the voxel-based analysis are 1394 msec and 23.6 ml/100 g/min, respectively. As a comparison, the mean transit time and perfusion are 1190 msec and 50.9 ml/g/min in whole brain gray matter.

In another aspect, techniques, apparatus and systems are described for implementing fast CBF estimation in multi-phase pseudo-continuous arterial spin labeling (MP-PCASL) using signal demodulation. The MP-PCASL method offers more robust cerebral blood flow (CBF) quantification than the conventional PCASL method and higher SNR than Pulsed ASL. In addition, it provides phase tracking errors at the tagging locations, which gives additional opportunities for measuring and optimizing the tagging efficiency of conventional PCASL. However, the MP-PCASL method uses a per-voxel fit to the nonlinear signal equation. The time needed for this nonlinear fitting procedure (about 5 minutes) can be problematic for applications such as optimized PCASL for functional MRI studies. A signal demodulation processing method for MP-PCASL is described that reduces the required processing time by two orders of magnitude, while providing comparable estimates of CBF and phase errors.

For MP-PCASL the phase increment between two successive RF pulses can be expressed by the equation: $\Delta\theta n = \gamma Gtd + 2\pi n/N$ (Eq. 11), where γ is the gyromagnetic ratio, G is the average gradient strength, t is the interval between RF pulses, d is the distance from the gradient center to tagging location, n denotes the nth phase, and N is the number of phases. Here γGtd is the phase tracking term and 2πn/N is the phase offset which generates different amounts of inversion.

Figure 22:
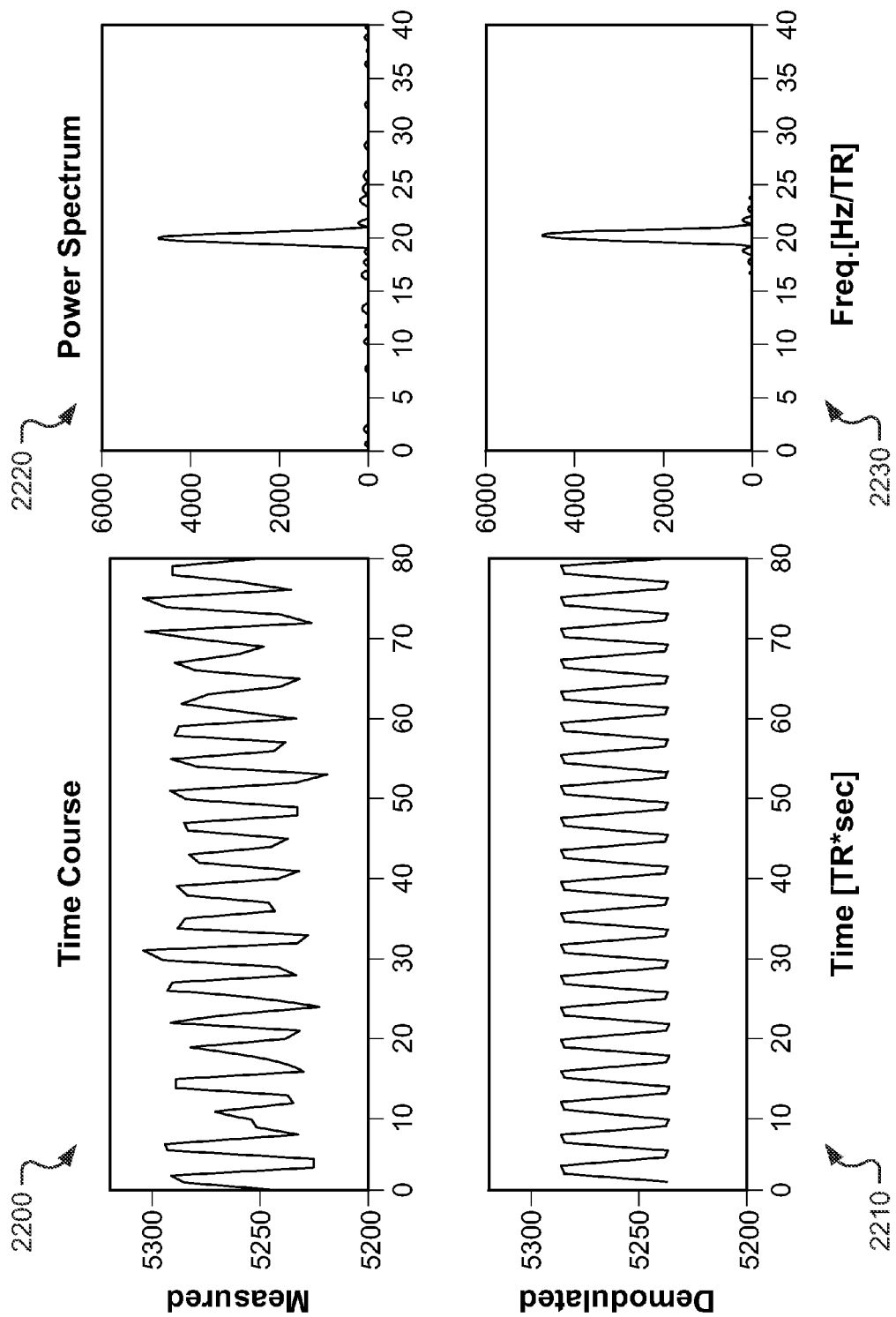
FIG. 22 shows a time course and its power spectrum from a single voxel (upper row) and those from the sinusoidal component at the frequency of the multiphase modulation (lower row).

FIG. 22 shows a time series from a voxel obtained with 4-phase PCASL and its power spectrum (upper row, 2200 and 2220). Because the power spectral density has a dominant component at the multi-phase frequency, the sinusoidal component at the multi-phase frequency (lower row, 2210 and 2230 of FIG. 22) contains most of the information in the MP-PCASL signal. Under the assumption that the inversion response to the phase offset is sinusoidal, the per-voxel basis multi-phase modulated time course (Si(t)) can be expressed as Eq. 12, where $a_i$ is the magnetization of arterial blood at ith voxel that has been delivered to the voxel (or ASL signal), $\theta_{offset}(t)$ is the phase offset at $t^{th}$ phase, εi is the phase tracking error, and bi is the baseline signal from static tissue. Because the modulated signal has the periodicity of the number of phases (m), a demodulation of the multi-phase frequency component (Eq. 13) can provide direct estimation of the multi-phase modulation: the magnitude and the phase of the demodulation can be interpreted as the ASL signal and the phase tracking errors, respectively, and the mean of the time course becomes the baseline signal from static tissues as shown in Eq. 14.

$$S_i(t) = a_i \cos(\theta_{offset}(t) - \varepsilon_i) + b_i \quad (12)$$

$$F_i(T/m) = \sum_{t=0}^{T-1} S_i(t) \cdot e^{-j2\pi \cdot t/m} \quad (13)$$

$$a_i = |F_i(T/m)|, \quad (14)$$
$$\varepsilon_i = \arg(F_i(T/m))$$
$$b_i = \frac{1}{T} \sum_{t=0}^{T-1} S_i(t)$$

The mean gray matter CBF values obtained using 4-phase PCASL are compared with the nonlinear fitting and the demodulation methods over 5 subjects (3 men and 2 women). The experiment was executed on a 3T Signa HDx scanner with an 8-channel head coil (GE Healthcare, Waukesha, Wis.). PCASL scan parameters were 1600 msec tag duration, 1000 ms post labeling delay, TR 3.6 sec, 80 reps. Imaging parameters included 24 cm FOV, 20 slices (5 mm thick, skip 1 mm), single-shot spiral acquisition (TE=3 ms), and 5 min. scan time. Mean gray matter CBF values and mean phase tracking errors were obtained from the gray matter mask, which was defined with a high resolution anatomical scan.

Figure 23:
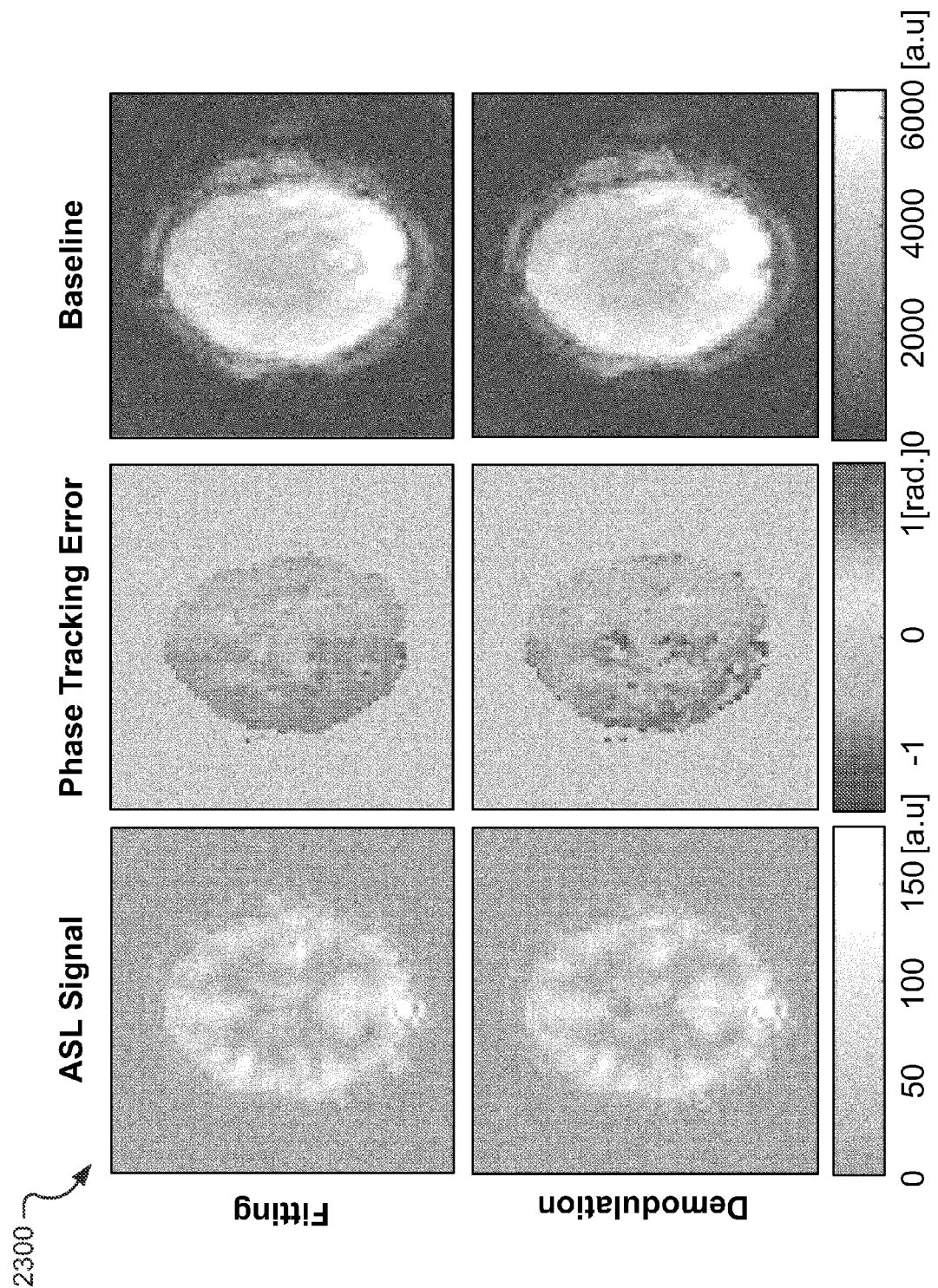
FIG. 23 shows an example of estimates of ASL signal, phase tracking error, and baseline signal with the two estimation methods.
Figure 25F:
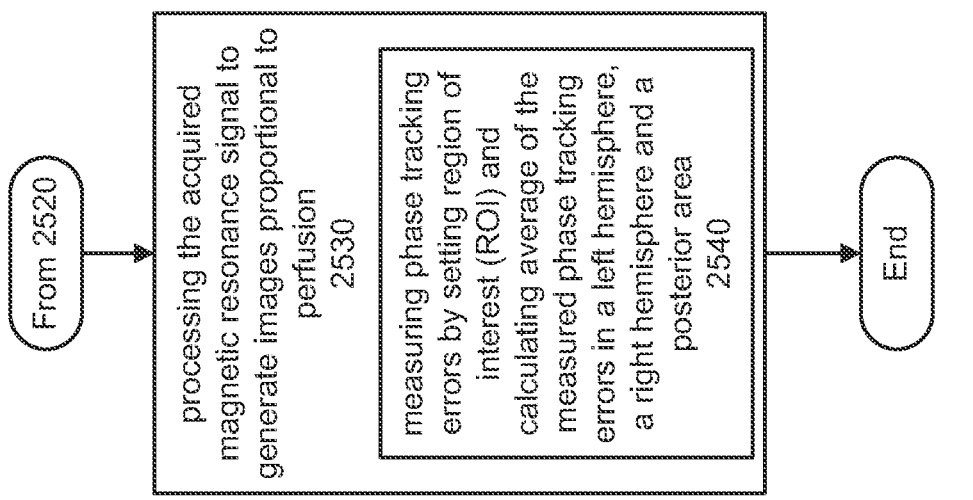
Figure 25E:
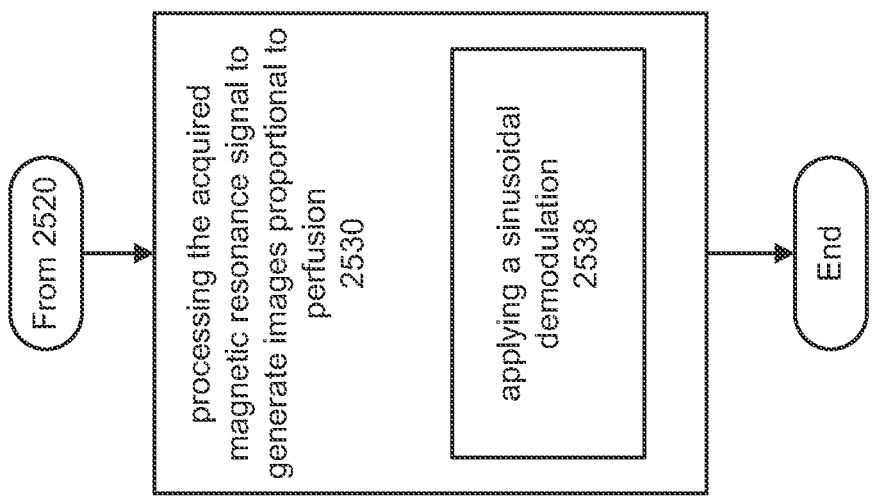
Figure 25D:
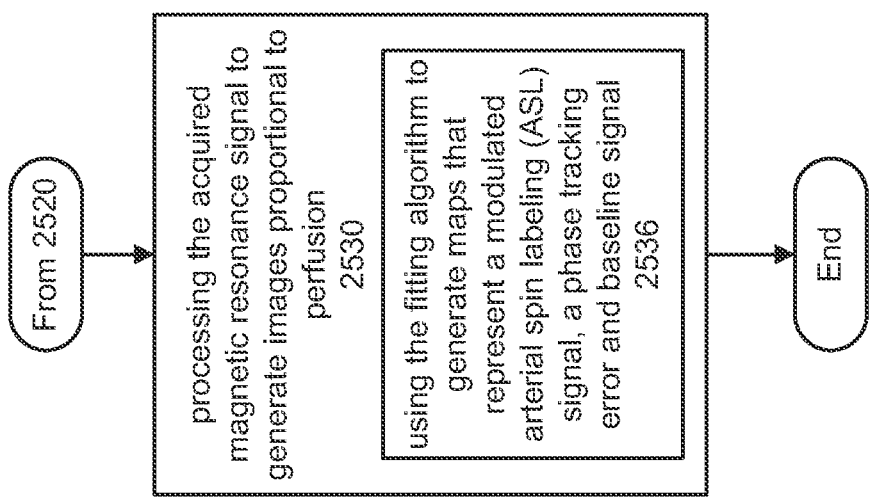
Figure 25I:
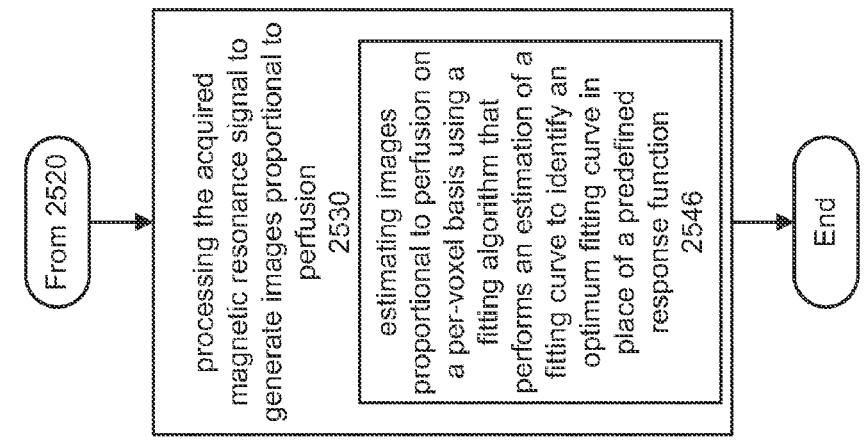
Figure 25H:
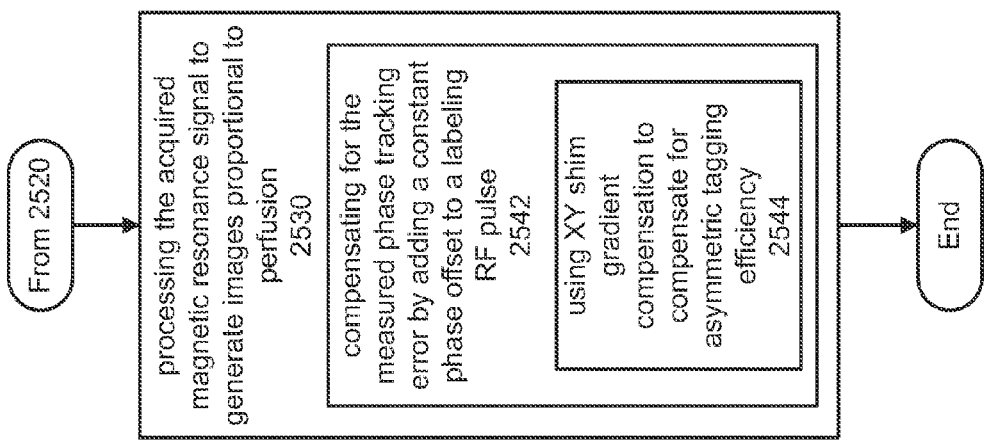
Figure 25G:
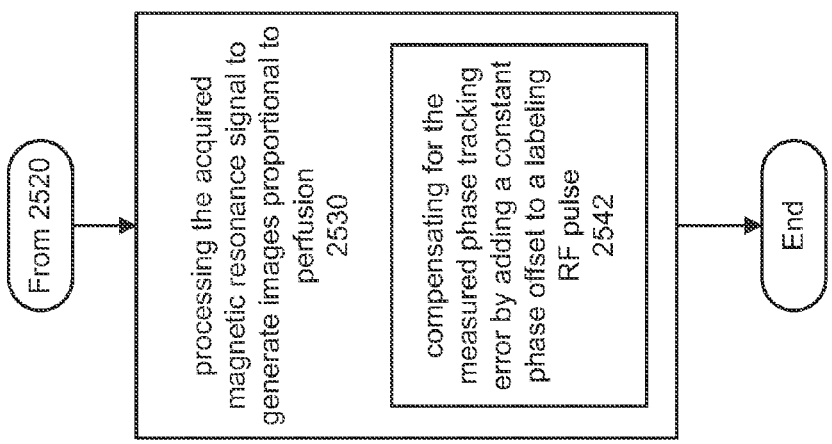
Figure 25J:
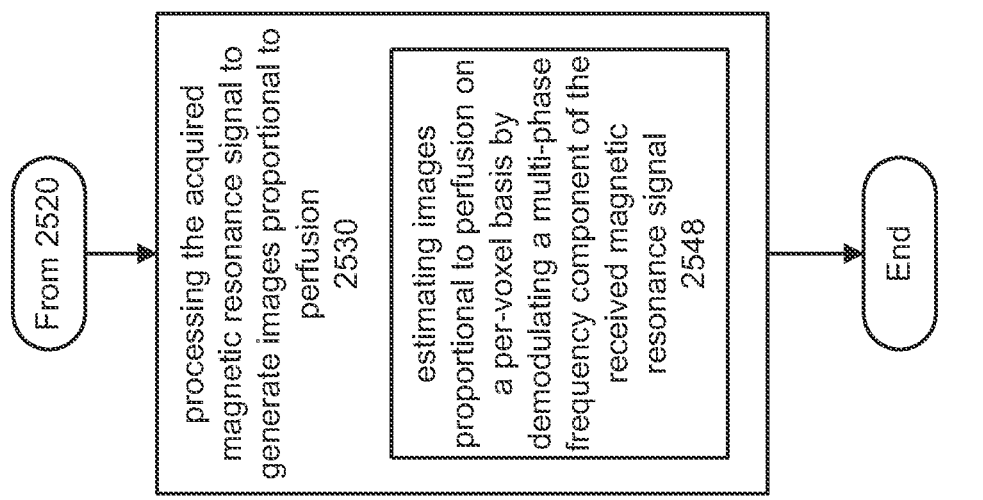

The proposed demodulation is much faster (<3 sec) than the conventional fitting method (~5 min). FIG. 23 shows an example 2300 of estimates of ASL signal, phase tracking error, and baseline signal with the two estimation methods. As shown in FIG. 23, the estimates of the ASL signal, the phase tracking error, and the baseline signal with the proposed demodulation method are comparable to that with the conventional fitting methods. The table 2400 in FIG. 24 presents the mean gray matter CBF values and measured tracking errors with two estimation methods and the differences. The demodulation method provided slightly lower values (average of 1% decrease) of CBF estimates since the side lobe in the power spectrum in actual inversion response was not considered in the demodulation.

FIGS. 25a, 25b, 25c, 25d, 25e, 25f, 25g, 25h, 25i and 25j are process flow diagrams for a process 2500 of performing a MP PCASL method as described in this specification. The method 2500 can include applying a gradient field and a train of RF pulses comprising more than two phases to tag a target blood vessel (2510); acquiring magnetic resonance signals based on the applied train of RF pulses to sample the more than two phases (2520); and processing the acquired magnetic resonance signal to generate images proportional to perfusion (2530).

The train of RF pulses can include at least four different phases with an evenly distributed phase offset. Also, processing the acquired magnetic resonance signals can include estimating phase tracking errors and compensating for the estimated phase tracking errors (2532). Processing the acquired magnetic resonance signal can include estimating images proportional to perfusion on a per-voxel basis using fitting algorithm with a predefined response function (2534). Processing the acquired magnetic resonance signal can include using the fitting algorithm to generate maps that represent a modulated arterial spin labeling (ASL) signal, a phase tracking error and baseline signal (2536). Processing the acquired magnetic resonance signal can include applying a sinusoidal demodulation (2538). Processing the acquired magnetic resonance signal can include measuring phase tracking errors by setting region of interest (ROI) and calculating average of the measured phase tracking errors in a left hemisphere, a right hemisphere and a posterior area (2540). Moreover, processing the acquired magnetic resonance signal can include compensating for the measured phase tracking error by adding a constant phase offset to a labeling RF pulse (2542). Compensating for the measure phase tracking error can include using XY shim gradient compensation to compensate for asymmetric tagging efficiency (2544). Processing the acquired magnetic resonance signal can include estimating images proportional to perfusion on a per-voxel basis using a fitting algorithm that performs an estimation of a fitting curve to identify an optimum fitting curve in place of a predefined response function (2546). Processing the acquired magnetic resonance signal can include estimating images proportional to perfusion on a per-voxel basis by demodulating a multiphase frequency component of the received magnetic resonance signal (2548). The processes 2532, 2534, 2536, 2538, 2540, 2542, 2544, 2546 and 2548 can be performed in combination or separately.

Tangible Useful Applications

The MP PCASL method can outperform the pulsed ASL and the conventional PCASL. Therefore, MP PCASL can replace existing ASL methods. For example, the optimized PCASL method described herein can be used for fMRI and other application which requires optimal tagging efficiency. Additionally, the described demodulation method can provide reliable CBF estimates while providing faster estimation time.

While this specification contains many specifics, these should not be construed as limitations on the scope of an invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or a variation of a subcombination.

The described systems, apparatus and techniques can be implemented in electronic circuitry, computer hardware, firmware, software, or in combinations of them, such as the structural means disclosed in this specification and structural equivalents thereof. This can include at least one computer-readable storage medium embodying a program operable to cause one or more data processing apparatus (e.g., a signal processing device including a programmable processor) to perform operations described. Thus, program implementations can be realized from a disclosed method, system, or apparatus, and apparatus implementations can be realized from a disclosed system, computer-readable medium, or method. Similarly, method implementations can be realized from a disclosed system, computer-readable medium, or apparatus, and system implementations can be realized from a disclosed method, computer-readable medium, or apparatus.

For example, the disclosed embodiments below can be implemented in various systems and apparatus, including, but not limited to, a special purpose data processing apparatus (e.g., a wireless access point, a remote environment monitor, a router, a switch, a computer system component, a medium access unit), a mobile data processing apparatus (e.g., a wireless client, a cellular telephone, a personal digital assistant (PDA), a mobile computer, a digital camera), a general purpose data processing apparatus (e.g., a minicomputer, a server, a mainframe, a supercomputer), or combinations of these.

Only a few implementations are disclosed. However, variations and enhancements of the disclosed implementations and other implementations can be made based on what is described and illustrated in this specification.

What is claimed is:

1. A magnetic resonance imaging (MRI) system, comprising:
    a means for applying a gradient field and a train of RF pulses to tag a target blood vessel, and
    a means for acquiring magnetic resonance signals resulting from the applied train of RF pulses by sampling at more than two phases; and
    a means for processing the acquired magnetic resonance signal to generate images proportional to perfusion.

2. The MRI system of claim 1 wherein the sampling at more than two phases comprises sampling at least four different phases with an evenly distributed phase offset.

3. The MRI system of claim 1, wherein the means for processing the received magnetic resonance signal is configured for estimating images proportional to perfusion on a per-voxel basis using fitting algorithm with a predefined response function.

4. The MRI system of claim 3, wherein the means for processing the received magnetic resonance signal is configured to use the fitting algorithm to generate maps that represent a modulated arterial spin labeling (ASL) signal, a phase tracking error and baseline signal.

5. The MRI system of claim 1, wherein the means for applying the gradient field includes a means for generating an encoded and slice-selective magnetic field.

6. A method of magnetic resonance imaging (MRI), comprising operations performed by an MRI system, the method comprising:
    applying a gradient field and a train of RF pulses to tag a target blood vessel;
    acquiring magnetic resonance signals resulting from the applied train of RF pulses by sampling at more than two phases; and
    processing the acquired magnetic resonance signal to generate images proportional to perfusion.

7. The method of claim 6, wherein the sampling at more than two phases comprises sampling at least four different phases with an evenly distributed phase offset.

8. The method of claim 6, wherein processing the acquired magnetic resonance signal comprises:
    estimating images proportional to perfusion on a per-voxel basis using fitting algorithm with a predefined response function.

9. The method of claim 8, wherein processing the acquired magnetic resonance signal comprises:
    using the fitting algorithm to generate maps that represent a modulated arterial spin labeling (ASL) signal, a phase tracking error and baseline signal.

10. The method of claim 6, wherein the applying the gradient field includes generating an encoded and slice-selective magnetic field.

11. A computer program product comprising a non-transitory computer-readable storage medium having instructions stored thereon and operable to cause a magnetic resonance imaging system to perform operations, comprising:
    applying a gradient field and a train of RF pulses to tag a target blood vessel;
    acquiring magnetic resonance signals resulting from the applied train of RF pulses by sampling at more than two phases; and
    processing the acquired magnetic resonance signal to generate images proportional to perfusion.

12. The non-transitory computer-readable storage medium of claim 11, wherein the sampling at more than two phases comprises at least four different phases with an evenly distributed phase offset.

13. The non-transitory computer-readable storage medium of claim 11, wherein the processing the acquired magnetic resonance signal comprises:
    estimating images proportional to perfusion on a per-voxel basis using fitting algorithm with a predefined response function.

14. The non-transitory computer-readable storage medium of claim 13, wherein the processing the acquired magnetic resonance signal comprises:
    using the fitting algorithm to generate maps that represent a modulated arterial spin labeling (ASL) signal, a phase tracking error and baseline signal.

15. The non-transitory computer-readable storage medium of claim 11, wherein the applying the gradient field includes generating an encoded and slice-selective magnetic field.

16. A method of performing magnetic resonance imaging, the method comprising:
    applying a control pulse sequence comprising a train of radio frequency (RF) pulses comprising:
        a gradient,
        RF amplitude waveforms, and
        an RF phase schedule;
    applying a tag pulse sequence comprising another train of RF pulses comprising:
        the gradient,
        the RF amplitude waveform, and
        another RF phase schedule different from the RF phase schedule for the control pulse sequence;
    acquiring magnetic resonance signals resulting from the applied train of RF pulses by sampling at more than two phases; and
    processing the acquired magnetic resonance signals to generate images proportional to perfusion.

17. The method of claim 16, wherein the sampling at more than two phases comprises sampling at least four different phases with an evenly distributed phase offset.

18. The method of claim 16, wherein processing the acquired magnetic resonance signal comprises:
    estimating images proportional to perfusion on a per-voxel basis using fitting algorithm with a predefined response function.

19. The method of claim 18, wherein processing the acquired magnetic resonance signal comprises:
    using the fitting algorithm to generate maps that represent a modulated arterial spin labeling (ASL) signal, a phase tracking error and baseline signal.

20. The method of claim 16, wherein the gradient comprises an encoded and slice-selective magnetic field.

* * * * *